US007928073B2

(12) United States Patent
Caput et al.

(10) Patent No.: US 7,928,073 B2
(45) Date of Patent: Apr. 19, 2011

(54) PURIFIED POLYPEPTIDES HAVING IL-13 RECEPTOR ACTIVITY

(75) Inventors: Daniel Caput, Avignolet-Lauragais (FR); Pascual Ferrara, Avignolet-Lauragais (FR); Patrick Laurent, Auterive (FR); Natalio Vita, Montgiscard (FR)

(73) Assignee: Sanofi-Aventis, Paris (FR)

( * ) Notice: Subject to any disclaimer, the term of this patent is extended or adjusted under 35 U.S.C. 154(b) by 1306 days.

(21) Appl. No.: 11/182,384

(22) Filed: Jul. 15, 2005

(65) Prior Publication Data

US 2006/0035855 A1 Feb. 16, 2006

(51) Int. Cl.
*A61K 38/16* (2006.01)
(52) U.S. Cl. ........................................ 514/21.2; 435/361
(58) Field of Classification Search ........................ None
See application file for complete search history.

(56) References Cited

U.S. PATENT DOCUMENTS

| 5,596,072 | A | 1/1997 | Culpepper et al. |
| 5,710,023 | A | 1/1998 | Collins et al. |
| 6,911,530 | B1 * | 6/2005 | Willson et al. ............ 530/387.1 |

OTHER PUBLICATIONS

Hilton et al PNAS 1996, vol. 93, pp. 497-501.*
Lefort et al, IL-13 and IL-4 share signal transduction elements as well as receptor components in TF-1 cells, FEBS Letters, vol. 336, No. 203, Jun. 12, 1995, pp. 122-126.
Vita et al., Characterization and Comparison of the Interleukin 13 Receptor with the Interleukin 4 Receptor on Several Cell Types, J. of Bio. Chem., vol. 270, No. 8, Feb. 24, 1995, pp. 3512-3517.
Obiri et al., Receptor for Interleukin 13, J. of Bio. Chem., vol. 270, No. 15, Apr. 14, 1995, pp. 8797-8804.
Zurawski et al., The Primary Binding Subunit of the Human Interleukin-4 Receptor Is Also a Component of the Interleukin-13 Receptor, J. of Bio. Chem., vol. 270, No. 23, Jun. 9, 1995.
Aman et al., cDNA Cloning and Characterization of the Human Interleukin 13 Receptor alpha Chain, J. of Bio. Chem., vol. 271, No. 46, Nov. 15, 1996, pp. 29265-29270.
Caput et al., Cloning and Characterization of a Specific Interleukin (IL-13) Binding Protein Structurally Related to the IL-5 Receptor alpha Chain, J. of Bio. Chem., vol. 271, No. 208, Jul. 12, 1996, pp. 16921-16926.
Callard et al., IL-4 and IL-13 receptors: are they one and the same?, Immunology Today, vol. 17, No. 3, Mar. 1996, pp. 108-110.
Wills-Karp, Interleukin-13: Central Mediator of Allergic Asthama, Immunology Today, vol. 17, No. 2, Mar. 1996.

* cited by examiner

*Primary Examiner* — Elly-Gerald Stoica
(74) *Attorney, Agent, or Firm* — J. Darrell Fontenot

(57) ABSTRACT

This invention relates to a purified polypeptide comprising an amino acid sequence chosen from the sequence SEQ ID NO:4 or biologically active amino acid sequences derived from SEQ ID NO:4.

3 Claims, 18 Drawing Sheets

FIG. 2A

```
GGTGCCTGTCGGGGGAGAGAGGCAATATCAAGGTTTAAATCTCGGAGAAATGGCT          58
                                                MetAla           2

TTCGTTTGGCTTGGCTATCGGATGCTTATATACCTTTCTGATAAGCACAACATTTGGCTGT   118    59
PheValCysLeuAlaIleGlyCysLeuTyrThrPheLeuIleSerThrThrPheGlyCys      22     3

ACTTCATCTTCAGACACCGAGATAAAAGTTAACCCTCCTCAGGATTTTGAGATAGTGGAT    178   119
ThrSerSerAspThrGluIleLysValAsnProProGlnAspPheGluIleValAsp         42    23

CCCGGATACTTAGGTTATCTCTATTTGGAATGGCAACCCACTGTCTCTGATCATTTT       238   179
ProGlyTyrLeuGlyTyrLeuTyrLeuGlnTrpGlnProProLeuSerLeuAspHisPhe      62    43

AAGGAATGCACAGTGGAATATGAACTAAAATACCGAAACATTGGTAGTAGGAAG          298   239
LysGluCysThrValGluTyrGluLeuLysTyrArgAsnIleGlySerGluTrpLys         82    63

ACCATCATTACTAAGAATTACATTACAAAGATGGGTTTGATCTTAACAAGGGCATTGAA    358   299
ThrIleIleThrLysAsnLeuHisTyrLysAspGlyPheAspLeuAsnLysGlyIleGlu     102    83

GCGAAGATACACACGCTTTACCATGGCAATGCACAAATGGATCAGAAGTCAAAGTTCC     418   359
AlaLysIleHisThrLeuProTrpGlnCysThrAsnGlySerGluValGlnSerSer       122   103

TGGGCAGAAACTACTTATTGGATATCACCAAGGAATTCCAGAAACTAAAGTTCAGGAT     478   419
TrpAlaGluThrThrTyrTrpIleSerProGlnGlyIleProGluThrLysValGlnAsp    142   123

ATGGATTGCGTATATTACAATTGGCAATATTTACTCTGTTCTTGGAAACCTGGCATAGGT   538   479
MetAspCysValTyrTyrAsnTrpGlnTyrLeuLeuCysSerTrpLysProGlyIleGly    162   143

GTACTTCTTGATACCAATTACAACTTGTTTTACTGGTATGAGGGCTTGGATCATGCATTA   598   539
ValLeuLeuAspThrAsnTyrAsnLeuPheTyrTrpTyrGluGlyLeuAspHisAlaLeu    182   163

CAGTGTGTAGATTACATCAAGGCTGATGGACAAAATATAGGATGCAGATTCCCTATTTG    658   599
GlnCysValAspTyrIleLysAlaAspGlyGlnAsnIleGlyCysArgPheProTyrLeu    202   183
```

FIG. 2B

```
 659 GAGGCATCAGACTATAAAGATTCTATATTGTGTTAATGGATCATCAGAGAACAAGCCT  718
 203 GluAlaSerAspTyrLysAspPheTyrIleCysValAsnGlyLysSerGluAsnLysPro 222

719 ATCAGATCCAGTTATTCACTTTCAGCTTCAAAATATAGTTAAACCTTTGCCGCCAGTC  778
 223 IleArgSerSerTyrPheThrPheGlnLeuGlnAsnIleValLysProLeuProProVal 242

779 TATCTTACTTTTACTCGGGAGAGTTCATGTGAAATTAAGCTGAAATGGAGCATACCTTTG  838
 243 TyrLeuThrPheThrArgGluSerSerCysGluIleLysLeuLysTrpSerIleProLeu 262

839 GGACCTATTCCAGCAAGGTGTTTGATTATGAAATTGAGATCAGAGAAGATGATACTACC  898
 263 GlyProIleProAlaArgCysPheAspTyrGluIleGluIleArgGluAspAspThrThr 282

899 TTGGTGACTGCTACAGTTGAAAATGAAACATACACCTTGAAACAACAAATGAAACCCGA  958
 283 LeuValThrAlaThrValGluAsnGluThrThrLeuLysThrThrAsnGluThrArg 302

959 CAATTATGCTTTGTAGTAAGAAGCAAAGTGAATATTATTGCTCAGATGACGGAATTTGG 1018
 303 GlnLeuCysPheValValArgSerLysValAsnIleIleTyrCysSerAspGlyIleTrp 322

1019 AGTGAGTGGAGTGATAAACAATGCTGGGAAGGTGAAGACCTATCGAAGAAAACTTTGCTA 1078
 323 SerGluTrpSerAspLysGlnCysTrpGluGlyGluAspLeuSerLysLysThrLeuLeu 342

1079 CGTTTCTGGCTACCATTTGGTTTCATCTTAATATTAGTTATATTTGTAACCGGTCTGCTT 1138
 343 ArgPheTrpLeuProPheGlyPheIleLeuIleLeuValIleLeuValThrGlyLeuLeu 362

1139 TTGCGTAAGCCAAACCACACCTACCCAAAAAATGATTCCAGAATTTTCTGTGATACATGAAGA 1198
 363 LeuArgLysProAsnThrTyrProLysMetIleProGluPhePheCysAspThr 380

1199 CTTTCCATATCAAGAGACATGGTATTGACTCAACAGTTTCCAGTCCATGGCCCAAATGTTCA 1258
1259 ATATGAGTCTCAATAAACTGAATTTTCTGCGAATGTTG 1298
```

FIG. 2C

```
IL13R   MAFVCLAIGCLYTFLISTTFGCTSSSDTEIKVNPPQDFEIVDPGYLGYLY      50
IL5R    ..MIIVAHVLLILLGATEILQADLLPDEKISLLPPVNFTIKVTG.LAQVL      47

IL13R   LQWQPPLSLDHFKECTVEYELKYRNIGSETWKTIITKNLHYKDGFDLNKG     100
IL5R    LQWKPNPDQEQ.RNVNLEYQVKINAPKEDDYETRITES...KCVTILHKG     93

IL13R   IEAKIHTLLPWQCTNGSEVQSSWAETTYWISPQGIPETKVQDMDCV.....   146
IL5R    FSASVRTILQ...NDHSLLASSWASAE.LHAPPGSPGTSIVNLTCTTNTT   139

IL13R   ..YYNWQ......YLICSWKPGIGVLLDTNYNLFYWYEGLDHALQCVDYIK   189
IL5R    EDNYSRLRSYQVSLHCTWLVGTDAPEDTQYFLYYRGSWTE..ECQEYSK    187

IL13R   AD.GQNIGCRFP..YLEASDYKDFYICVNGSSENKPIRSSYFTFQLQNIV   236
IL5R    DTLGRNIACWFPRTFILSKGRDWLSVLVNGSSKHSAIRPFDQLFALHAID  237
```

FIG. 2D

```
IL13R                                                          
IL5R   KPLPPVYLTFTRESSCEIKLKWSIPLGPIPARCFDYEIEIREDDTTLVTA  286
       QINPPLNVTAEIEGT.RLSIQWEKPVSAFPIHCFDYEVKIHNTRNGYLQI   286

IL13R  TVENETYTLKTTNETRQLCFVVRSKVNIYCSDDGI|WSEWS|DKQCWEGEDL 336
IL5R   EKLMTNAFISIIDDLSKYDQVRAAVSSMCREAGI|WSEWS|Q.PIYVGNDE  335

IL13R  SKKTLLRFWLPFGFILILVIFVTGLLLRKPNTYPKMIP........EF     376
IL5R   HKPLREWFVIVIMATICFILILSLICKICHLWIKLFPPIPAPKSNIKDL    385

IL13R  FCDT..........................................  380
IL5R   FVTTNYEKAGSSETEIEVICYIEKPGVETLEDSVF             420
```

FIG. 7A

```
1    TCAGCCCCGGCCGGGGCTCCGAGGGCTGCATGGAGTGGCCGGCCCGGCTCTGCGGG      60
                                M  E  W  P  A  R  L  C  G         9
61   CTGTGGGCGCTGCTGCTCGCGGGGGGCGGGGCCGCGCCGACGCCCGCGCCTACG       120
     L  W  A  L  L  L  A  G  G  G  G  A  A  P  T               29
121  GAAACTCAGCCACCTGTGACAAATTTGAGTGTCTCTGTGAAAACCTCTGCACAGTAATA  180
     E  T  Q  P  P  V  T  N  L  S  V  E  N  L  C  T  V  I       49
181  TGGACATGGAATCCACCCGAGGAGCCAGCTCAAATTGTAGTCTATGGTATTTAGTCAT   240
     W  T  W  N  P  P  E  G  A  S  S  N  C  S  L  W  Y  F  S  H  69
241  TTTGGGCGACAAACAAGATAAGAAAATAGCTCCGGAAACTCGTCGTTCAATAGAAGTACCC 300
     F  G  D  K  Q  D  K  K  I  A  P  E  T  R  R  S  I  E  V  P  89
301  CtGAATGAGAGGATTTGTCTGCAAGTGTCCCAGTGTAGCACCATGAGAGTGAGAAG      360
     L  N  E  R  I  C  L  Q  V  S  Q  C  S  T  N  E  S  E  K    109
361  CCTAGCATTTGGTTGAAAATGCATCTCACCCCAGAAGGTGATCCTGAGTCTGCTGTG    420
     P  S  I  L  V  E  K  C  I  S  P  P  E  G  D  P  E  S  A  V 129
421  ACTGAGCTTCAATGCATTTGGCACACTACATGAAGTCGTGTTCTTGGCTCCCCTGGA    480
     T  E  L  Q  C  I  W  H  N  L  S  Y  M  K  C  S  W  L  P  G 149
481  AGGAATACCAGTCCCGACACTATACTCTACTATTGGCACAGAAGCCTGGAAAAA       540
     R  N  T  S  P  D  T  Y  Y  W  H  R  S  L  E  K            169
541  ATTCATCAATGTGAAAACATCTTTAGAGAAGGCCAATACTTTGGTTGCTCTTTGATCTG  600
     I  H  Q  C  E  N  I  F  R  E  G  Q  Y  F  G  C  S  F  D  L 189
601  ACCAAAGTGAAGGATTCCAGTTTtGAACAACACAGTGTCCAAATAATGGTCAAGGATAAT 660
     T  K  V  K  D  S  S  F  E  Q  H  S  V  Q  I  M  V  K  D  N 209
```

FIG. 7B

```
 661  GCAGGAAAAATTAAACCATCCTTCAATATAGTGCCTTTAACTTCCCGTGTGAAACCTGAT   720
 210   A  G  K  I  K  P  S  F  N  I  V  P  L  T  S  R  V  K  P  D    229
 721  CCTCCACATATTAAAAACCTCCTTCCACATGATGACCTATATGTGCAATGGGAGAAT      780
 230   P  P  H  I  K  N  L  S  F  H  N  D  D  L  Y  V  Q  W  E  N    249
 781  CCACAGAATTTTATTAGCAGATGCCTATTTTATGAAGAGTACAATAACAGCCAAACT      840
 250   P  Q  N  F  I  S  R  C  L  F  Y  E  V  E  V  N  N  S  Q  T    269
 841  GAGACACACATAAATGTTTTCTACGTCCAAGAGGCTAAATGTGAGAATCCAGAATTTGAGAGA  900
 270   E  T  H  N  V  F  Y  V  Q  E  A  K  C  E  N  P  E  F  E  R    289
 901  AATGTGGAGAATACATCTTGTTTTCATGGTCCCCTGGTGTTCCTGATACTTGAACACA     960
 290   N  V  E  N  T  S  C  F  M  V  P  G  V  L  P  D  T  L  N  T    309
 961  GTCAGAATAAGAGTCAAAACAATAAGTTATGCTGTTATGAGGATGACAAACTCTGGAGTAAT 1020
 310   V  R  I  R  V  K  T  N  K  L  C  Y  E  D  D  K  L  W  S  N    329
1021  TGGAGCCAAGAAATGAGTATAGGTAAGAAGCGCAATGTCGCAGGTGCAATCATAGTACTCC 1080
 330   W  S  Q  E  M  S  I  G  K  K  R  N  S  T  L  Y  I  T  M  L    349
1081  CTCATTGTTCCAGTGATTATATTCCCTCCAATTCCTGATCCTGGCAAGATTTTAAAGAATGTTT 1140
 350   L  I  V  P  V  I  V  A  G  A  I  V  L  L  L  Y  L  K  R       369
1141  CTCAAGATTATTATTATTCCCTCCAATTCCTGATCCTGGCAAGATTTTTAAAGAATGTTT   1200
 370   L  K  I  I  F  P  P  I  P  D  D  P  G  K  I  F  K  E  M  F    389
1201  GGAGACCAGAATGATGATACTCTGCACTGGAAGAAGTACGACATCTATGAGAAGCAAACC    1260
 390   G  D  Q  N  D  D  T  L  H  W  K  K  Y  D  I  Y  E  K  Q  T    409
1261  AAGGAGGAAACCGACTCTGTAGTGCTGATAGAAAACCTGAAGAAAGCCTCAGTGATGG     1320
 410   K  E  E  T  D  S  V  V  L  I  E  N  L  K  K  A  S  Q  *       429
```

FIG. 7C

```
1381  TATCTGGAACTTATTAAATGGAAACTGAAACTGCACCATTAAAAACAGGCAGCTC  1440
1441  ATAAGAGCCACAGGTCTTTATGTTGAGTCGCCGCGAAAAACTAAAAATAATGGGCGCT  1500
1501  TTGGAGAAGAGTGTGGAGTCATTCTCATTGAATTATAAAGCCAGCAGGCTTCAAACTAG  1560
1561  GGGACAAAGCAAAAAGTGATAGTGTGGAGTTCTTTGTGTTCTTTGTCAACATGAGTTGTGACAACT  1620
1621  TCCTGAGGGATCTATACTTGCTTGTGGTGCAAATGCTAAATGTCAAACTTGAGTCACAAAGAACAATTTATTTGT  1680
1681  AGGGAACTCATTTGGGGTGCAAATGCTAAATGTCAAACTTGAGTCACAAAGAACATGTAG  1740
1741  AAAACAAAATGGATAAAATCTGATATGTATTGTTTGGGATCCTATTGAACCATGTTGTG  1800
1801  GCTATTAAACTCTTTAACAGTCTGGGCTGGGTCCGGTCCGAGTTCCAGGCCTGTAATCCCAG  1860
1861  CAATTTGGGAGTCCGAGGCGGCGGATCACTGAGGTCAGGAGTTCAAGACCAGCCTGAC  1920
1921  CAAAATGGTGAAACTCCGTCTACTAAAACTACAAAAATTAACTGGGTGTGGTGGCGCG  1980
1981  TGCCTGTAATCCCAGCTACTCGGGAAGCTGAGGCAGGTGAATTGTTGTTGAACCTGGGAGGT  2040
2041  GGAGGTTGCAGTGAGCCAGAGATCACACCACTGCACTCTAGCCTGGGTGACAGAGCAAGAC  2100
2101  TCTGTCTAAAACAAAACAAAACAAAACAAAACCTCTTAATATTCTGAGT  2160
2161  CATCATTCCCTTCGACAGCATTTCCCTGCTTTGAAAGCCCCAGAAATCAGTGTTGGCC  2220
2221  ATGATGACAACTACAGAGAAAAACCAGAGGCAGCTTCTTGCCAGCCTTTCAAAGCCATT  2280
2281  TTAGGCTGTTAGGGCAGTGGAGGTAgAATGACTCCTGCTACTCAAGTAGCATTTACTGTGTCTTT  2340
2341  AAGTCTCTAACAATGTaTTTCTCACCCTCTGCTACTCAAGTAGCATTTACTGTGTCTTT  2400
2401  GGTTTGTGCTAGGCCCCCGGGTGTGCCAGTTCTGCCACTGAAGCACAGAGACCCCCTTCCCAGGGTTACAGTCTATt  2460
2461  TGAGACTCCTCAGTTCTTGACTTTCATTGCATTCTCCTTTGCATTCCCTTCCCTT  2520
2521  TTTAACTCCTCAATTGACTTTGACTTTAGCATCTGATTTCCCTTTGCATGTAAATCGTAGGATGTGAATCGCTCAGAAACAATGACTAATCT  2580
2581  GTAGCCTTTGACTTTAGCATCTGATTTGACTTTAAGTGTAAGTTAAGTGTGAATCTGCTCAGAAACAATGACTAATCT  2640
2641  CAGAGGATAATTAGCATTGATGAGGGTAAGTTAAGTGTGAATCTGCTCAGAAACAATGACTAATCT  2700
2701  TGCATATTTTGTAACTTCCATGTGAGGGTTTTCAGCATTGATATTTGTGCATTTCTAAA  2760
```

FIG. 7D

```
2761  CAGAGATGAGGTGGTATCTTCACGTAGAACATTGGTATTCGCTTGAGAAAAAGAATAG  2820
2821  TTGAACCTATTCTCTTCTTTACAAGATGGGTCCAGGATTCCTCCTTTCTCTGCCATAA  2880
2881  ATGATTAATTAAATAGCTTTTGTGTCTTACATTGGTAGCCAGCCAAGGCTCTGTTT   2940
2941  ATGCTTTTGGGGCATATATTGGGTTCCATTCTCACCTATCCACACAACATATCCGTAT  3000
3001  ATATCCCCTCTACTCTTCTCCCTCACACAGAAGTATGGGAAATGAGAGGCATTT     3060
3061  CCCCCACCCCATTTCTCTCCCTCACACACAGACTCATATTACTGGTAGGAACTTGAGAACT 3120
3121  TTATTTCCAAGTTGTTCAAACATTACCAGAATAATACAATGATGCTATTTGCAAT    3180
3181  TCCTGCTCCTAGGGAGGGAGATAAGAAAACCCTCACTCTCTACAGGTTTGGGTACAAGT 3240
3241  GGCAACCTGCTCCATGGCAGATGTAGAAGCATGGTGCCCTGGCTTCTCTGAGGAAGCTGG 3300
3301  GGTTCATGACAATGTTCTACTTTGTCTGTGTCTAGAAAGAATATTGGTTTTCCTGT    3360
3361  CCGTAGTAGATGTTCTACTTTCTGCTGTTCTCCAGGTATTTATAATTCTGGGAAGCAAAACCCATGC 3420
3421  ATAGGAATGAGATTAATTCCTTTCCAGGTATTTTATAATTCTGGAAGCAAAACCCATGC 3480
3481  CTCCCCTAGCCATTTTACTGTTATCCTATTTAGATGGCCATGAAGAGGATGCTGTGAA  3540
3541  ATTCCCAACAAACATTGATGCTGACAGTCAGTCGGAGTAGTCTGGGAAGTGATCTTT   3600
3601  GTTCCCATCCTCTTCTTTTTAGCAGTAAAATAGCTGAGGGAAAAGGAGGAAAAGGAAGT 3660
3661  TATGGGAATACCTGTGGTGGTTGTGATCCCTGTGGGAAATTAGTCTTGGAGCTCTTGGAGGTGTCTGT 3720
3721  ATCAGTGTGGATTTCCCATCCCTGTCCTAACATACCTAAGCAAACCCAGTGTCAGGATGGTAATTCTT 3780
3781  GCCTATGTGGATTTTTTCCTAACATACCTAAGCAAACCCAGTGTCAGGATGGTAATTCTT 3840
3841  ATTCTTTCGTTCAGTTAAGTTTTCCCTTCATCTGGGCACTGTTTCTGTTAACTGTGAAACAA  3900
3901  TGTTAACATTTTGGTAGTCTTCAACCAGGATTGTTTCTGTTAACTTCTTATAGGAAA  3960
3961  GCTTGAGTAAAATAAATATTGTCTTTTGTATGTCACCCaaaaaaaaaa  4009
```

FIG. 7E

```
                    IL-13α Mouse ─────┐
                    IL-13α Human ───┐ │
                                    │ ↓
                                    ↓
  1   MEWPARLCGLWALLLCAGGGGGGAAPTETQPPVTNLSVSVENLCTVIW   50
      |.::.||| |.||:::||       ..::.||:||||||||||||:||
  1   MARPALLGELLVLLL..WTATVGQVAAATEVQPPVTNLSVSVENLCTIIW  48

51   TWNPPEGASSNCSLWYFSHFGDKQDKKIAPETRRSIEVPLNERICLQVGS  100
      ||.|||||:||.||||||||..|:||||||||:|||.:|||.:|||||||
 49   TWSPPEGASPNCTLRYFSHFDDQQDKKIAPETHRKEELPLDEKICLQVGS   98

101   QCSTNESEKPSILVEKCISPPEGDPESAVTELQCIWHNLSYMKCSWLPGR  150
      ||| ||||||:|| ||||||||||||||||||||||||||||||||||||
 99   QCSANESEKPSLVKKCISPPEGDPESAVTELKCIWHNLSYMKCSWLPGR   148

151   NTSPDTNYTLYYWHRSLEKIHQCENIFREGQYFGCSFDLTKVKDSSFEQH  200
      ||||||:|||||| ::||||:|||||.:|||  |:||:|||.  :|.|:
149   NTSPDTHYTLYYWYSSLEKSRQCENIYREGQHIACSFKLTKV.EPSFEHQ  197

201   SVQIMVKDNAGKIKPSENIVPLTSRVKPDPPHIKNLSFHNDDLYVQWENP  250
      .|||||||||||:|||.|||.|:|||||||||||:| |:|..|||||:||
198   NVQIMVKDNAGKIRPSCKIVSLTSYVKPDPPHIKHLLLKNGALLVQWKNP   247
```

FIG. 7F

```
                                                      IL-13α Mouse ─┐
                                                      IL-13α Human ─┼─┐
                                                                    ↓ ↓
251 QNFISRCLFYEVEVNNSQTETHNVFYVQEAKCENPEFERNVENTSCFMVP 300
    ||||||||:|||:||||||:|:|||||::|:::|||:|::||||:||:
248 QNFRSRCLTYEVEVNNTQTDRHNILEVEEDKCQNSESDRNMEGTSCFQLP 297

301 GVLPDTLNTVRIRVKTNKLCYEDDKL[WSNWSQEMSIGKKRNSTLYITMLL] 350
    |||:||||||:|||:||||||:||:[::|:||:||||:||||:|||||||]
298 GVLADAVYTVRVRVKTNKLCFDDNKL[WSDWSEAQSIGKEQNSTFYTTMLL] 347

351 IVPVIVAGAIIVLLLYLKRLKIIIFPPIPDPGKIFKEMFGDQNDDTLHWK 400
    ::|:|:|:|:||::|||||||||||||||||||||||||||||||||||
348 TIPVFVAVAVILLFYLKRLKIIIFPPIPDPGKIFKEMFGDQNDDTLHWK 397

401 KYDIYEKQTKEETDSVVLIENLKKASQ 427
    |||||||||:|||||||||||||||::
398 KYDIYEKQSKEETDSVVLIENLKKAAP 424
```

FIG. 8A
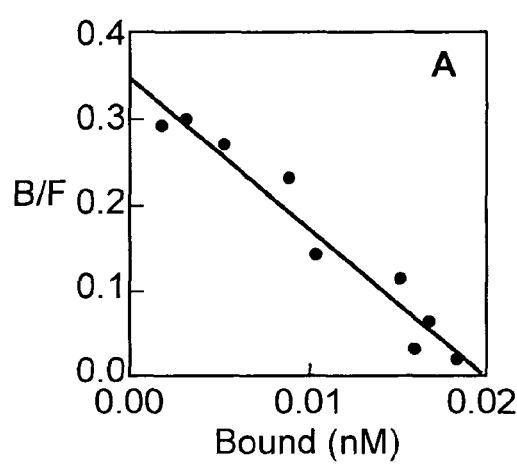
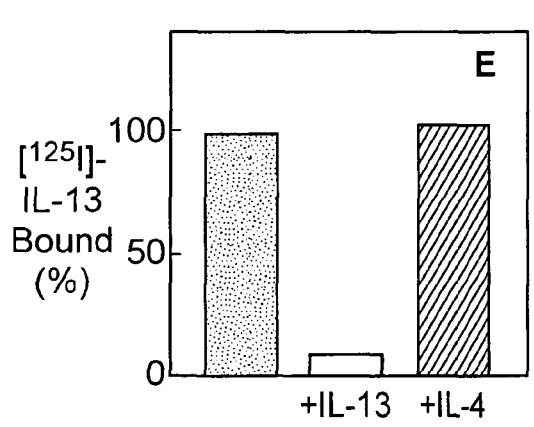
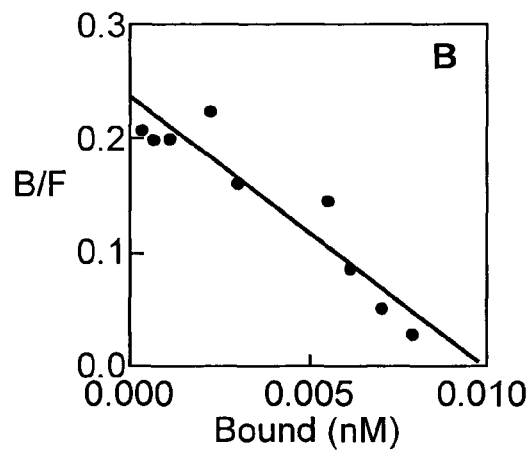
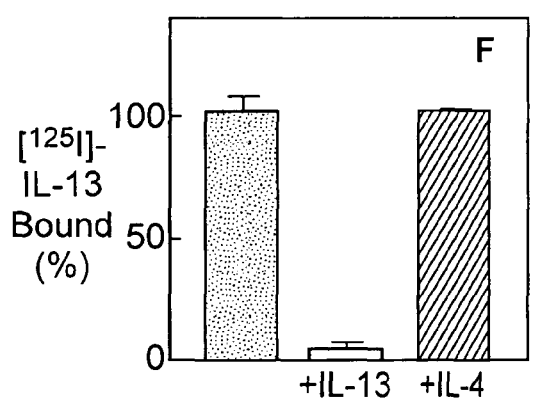

FIG. 8B
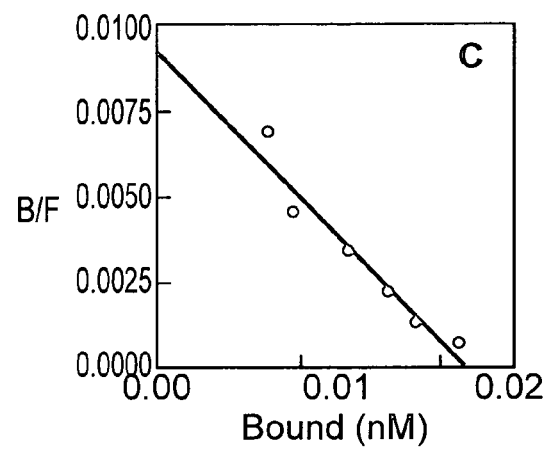
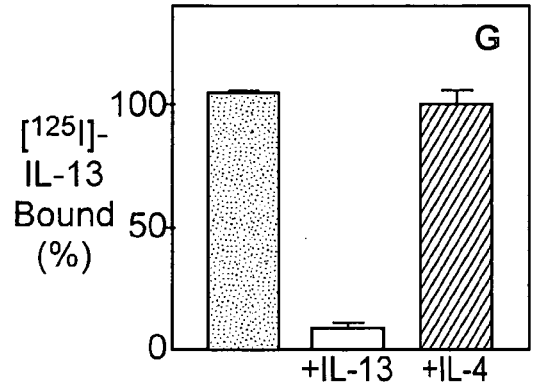
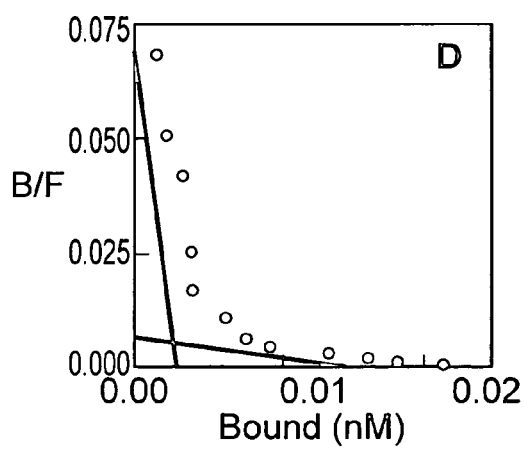
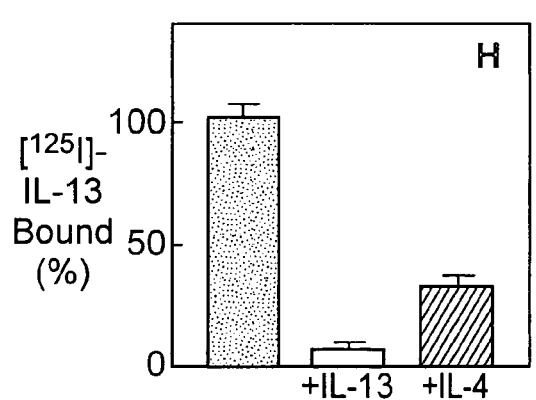

SEQUENCE LISTING

<160> NUMBER OF SEQ ID NOS: 16

<210> SEQ ID NO 1
<211> LENGTH: 1298
<212> TYPE: DNA
<213> ORGANISM: homo sapiens

<400> SEQUENCE: 1

```
ggtgcctgtc ggcggggaga gaggcaatat caaggtttta aatctcggag aaatggcttt      60
cgtttgcttg gctatcggat gcttatatac ctttctgata agcacaacat ttggctgtac     120
ttcatcttca gacaccgaga taaaagttaa ccctcctcag gattttgaga tagtggatcc     180
cggatactta ggttatctct atttgcaatg gcaaccccca ctgtctctgg atcattttaa     240
ggaatgcaca gtggaatatg aactaaaata ccgaaacatt ggtagtgaaa catggaagac     300
catcattact aagaatctac attacaaaga tgggtttgat cttaacaagg gcattgaagc     360
gaagatacac acgcttttac catggcaatg cacaaatgga tcagaagttc aaagttcctg     420
ggcagaaact acttattgga tatcaccaca aggaattcca gaaactaaag ttcaggatat     480
ggattgcgta tattacaatt ggcaatattt actctgttct tggaaacctg gcataggtgt     540
acttcttgat accaattaca acttgtttta ctggtatgag ggcttggatc atgcattaca     600
gtgtgttgat tacatcaagg ctgatggaca aaatatagga tgcagatttc cctatttgga     660
```

```
ggcatcagac tataaagatt tctatatttg tgttaatgga tcatcagaga acaagcctat    720
cagatccagt tatttcactt ttcagcttca aaatatagtt aaacctttgc cgccagtcta    780
tcttactttt actcgggaga gttcatgtga aattaagctg aaatggagca tacctttggg    840
acctattcca gcaaggtgtt ttgattatga aattgagatc agagaagatg atactacctt    900
ggtgactgct acagttgaaa atgaaacata caccttgaaa acaacaaatg aaacccgaca    960
attatgcttt gtagtaagaa gcaaagtgaa tatttattgc tcagatgacg gaatttggag   1020
tgagtggagt gataaacaat gctgggaagg tgaagaccta tcgaagaaaa ctttgctacg   1080
tttctggcta ccatttggtt tcatcttaat attagttata tttgtaaccg gtctgctttt   1140
gcgtaagcca aacacctacc caaaaatgat tccagaattt ttctgtgata catgaagact   1200
ttccatatca agagacatgg tattgactca acagtttcca gtcatggcca atgttcaat    1260 atgagtctca ataaactgaa ttttttcttgc gaatgttg                          1298
```

<210> SEQ ID NO 2
<211> LENGTH: 380
<212> TYPE: PRT
<213> ORGANISM: Homo sapiens

<400> SEQUENCE: 2

```
Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
                20                  25                  30

Asn Pro Pro Gln Asp Phe Glu Ile Val Asp Pro Gly Tyr Leu Gly Tyr
                35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
                100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
                180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270
```

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
            290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
                340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr
            370                 375                 380

<210> SEQ ID NO 3
<211> LENGTH: 4009
<212> TYPE: DNA
<213> ORGANISM: Homo sapiens

<400> SEQUENCE: 3

| | | | | | |
|---|---|---|---|---|---|
| tcagcccggc | cgggctccga | ggcgagaggc | tgcatggagt | ggccggcgcg | gctctgcggg | 60 |
| ctgtgggcgc | tgctgctctg | cgccggcggc | ggggcggg | gcggggcgc | cgcgcctacg | 120 |
| gaaactcagc | cacctgtgac | aaatttgagt | gtctctgttg | aaaacctctg | cacagtaata | 180 |
| tggacatgga | atccacccga | gggagccagc | tcaaattgta | gtctatggta | ttttagtcat | 240 |
| tttggcgaca | aacaagataa | gaaaatagct | ccggaaactc | gtcgttcaat | agaagtaccc | 300 |
| ctgaatgaga | ggatttgtct | gcaagtgggg | tcccagtgta | gcaccaatga | gagtgagaag | 360 |
| cctagcattt | tggttgaaaa | atgcatctca | cccccagaag | gtgatcctga | gtctgctgtg | 420 |
| actgagcttc | aatgcatttg | gcacaacctg | agctacatga | agtgttcttg | gctccctgga | 480 |
| aggaatacca | gtcccgacac | taactatact | ctctactatt | ggcacagaag | cctggaaaaa | 540 |
| attcatcaat | gtgaaaacat | ctttagagaa | ggccaatact | ttggttgttc | ctttgatctg | 600 |
| accaaagtga | aggattccag | ttttgaacaa | cacagtgtcc | aaataatggt | caaggataat | 660 |
| gcaggaaaaa | ttaaaccatc | cttcaatata | gtgcctttaa | cttcccgtgt | gaaacctgat | 720 |
| cctccacata | ttaaaaacct | ctccttccac | aatgatgacc | tatatgtgca | atgggagaat | 780 |
| ccacagaatt | ttattagcag | atgcctattt | tatgaagtag | aagtcaataa | cagccaaact | 840 |
| gagacacata | atgttttcta | cgtccaagag | gctaaatgtg | agaatccaga | atttgagaga | 900 |
| aatgtggaga | atacatcttg | tttcatggtc | cctggtgttc | ttcctgatac | tttgaacaca | 960 |
| gtcagaataa | gagtcaaaac | aaataagtta | tgctatgagg | atgacaaact | ctggagtaat | 1020 |
| tggagccaag | aaatgagtat | aggtaagaag | cgcaattcca | cactctacat | aaccatgtta | 1080 |
| ctcattgttc | cagtcatcgt | cgcaggtgca | atcatagtac | tcctgcttta | cctaaaaagg | 1140 |
| ctcaagatta | ttatattccc | tccaattcct | gatcctggca | agatttttaa | agaaatgttt | 1200 |
| ggagaccaga | atgatgatac | tctgcactgg | aagaagtacg | acatctatga | aagcaaacc | 1260 |
| aaggaggaaa | ccgactctgt | agtgctgata | gaaaacctga | gaaagcctc | tcagtgatgg | 1320 |
| agataattta | tttttacctt | cactgtgacc | ttgagaagat | tcttcccatt | ctccatttgt | 1380 |
| tatctgggaa | cttattaaat | ggaaactgaa | actactgcac | catttaaaaa | caggcagctc | 1440 |
| ataagagcca | caggtctta | tgttgagtcg | cgcaccgaaa | aactaaaaat | aatgggcgct | 1500 |

```
ttggagaaga gtgtggagtc attctcattg aattataaaa gccagcaggc ttcaaactag    1560
gggacaaagc aaaaagtgat gatagtggtg gagttaatct tatcaagagt tgtgacaact    1620
tcctgaggga tctatacttg ctttgtgttc tttgtgtcaa catgaacaaa ttttatttgt    1680
aggggaactc atttggggtg caaatgctaa tgtcaaactt gagtcacaaa gaacatgtag    1740
aaaacaaaat ggataaaatc tgatatgtat tgtttgggat cctattgaac catgtttgtg    1800
gctattaaaa ctcttttaac agtctgggct gggtccggtg gctcacgcct gtaatcccag    1860
caatttggga gtccgaggcg ggcggatcac tcgaggtcag gagttccaga ccagcctgac    1920
caaaatggtg aaaccctcctc tctactaaaa ctacaaaaat taactgggtg tggtggcgcg    1980
tgcctgtaat cccagctact cgggaagctg aggcaggtga attgtttgaa cctgggaggt    2040
ggaggttgca gtgagcagag atcacaccac tgcactctag cctgggtgac agagcaagac    2100
tctgtctaaa aacaaaaca aaacaaaaca aaacaaaaaa acctcttaat attctggagt    2160
catcattccc ttcgacagca ttttcctctg ctttgaaagc cccagaaatc agtgttggcc    2220
atgatgacaa ctacagaaaa accagaggca gcttctttgc caagaccttt caaagccatt    2280
ttaggctgtt aggggcagtg gaggtagaat gactccttgg gtattagagt ttcaaccatg    2340
aagtctctaa caatgtattt tcttcacctc tgctactcaa gtagcattta ctgtgtcttt    2400
ggtttgtgct aggcccccgg gtgtgaagca cagacccctt ccaggggttt acagtctatt    2460
tgagactcct cagttcttgc cactttttt tttaatctcc accagtcatt tttcagacct    2520
tttaactcct caattccaac actgattccc cctttgcat tctccctcct tcccttcctt    2580 gtagccttt gactttcatt ggaaattagg atgtaaatct gctcaggaga cctggaggag    2640
cagaggataa ttagcatctc aggttaagtg tgagtaatct gagaaacaat gactaattct    2700
tgcatatttt gtaacttcca tgtgagggtt ttcagcattg atatttgtgc attttctaaa    2760
cagagatgag gtggtatctt cacgtagaac attggtattc gcttgagaaa aaaagaatag    2820
ttgaacctat ttctctttct ttacaagatg gtccaggat tcctcttttc tctgccataa    2880
atgattaatt aaatagcttt tgtgtcttac attggtagcc agccagccaa ggctctgttt    2940
atgcttttgg ggggcatata ttgggttcca ttctcaccta tccacacaac atatccgtat    3000
atatcccctc tactcttact tcccccaaat ttaaagaagt atgggaaatg agaggcattt    3060 ccccccacccc atttctctcc tcacacacag actcatatta ctggtaggaa cttgagaact    3120
ttatttccaa gttgttcaaa catttaccaa tcatattaat acaatgatgc tatttgcaat    3180
tcctgctcct aggggagggg agataagaaa ccctcactct ctacaggttt gggtacaagt    3240
ggcaacctgc ttccatggcc gtgtagaagc atggtgccct ggcttctctg aggaagctgg    3300
ggttcatgac aatggcagat gtaaagttat tcttgaagtc agattgaggc tgggagacag    3360
ccgtagtaga tgttctactt tgttctgctg ttctctagaa agaatatttg gttttcctgt    3420
ataggaatga gattaattcc tttccaggta tttttataatt ctgggaagca aaacccatgc    3480 ctcccccctag ccatttttac tgttatccta tttagatggc catgaagagg atgctgtgaa    3540
attcccaaca acattgatg ctgacagtca tgcagtctgg gagtgggaa gtgatctttt    3600 gttcccatcc tcttctttta gcagtaaaat agctgaggga aagggaggg aaaaggaagt    3660 tatgggaata cctgtggtgg ttgtgatccc taggtcttgg gagctcttgg aggtgtctgt    3720
atcagtggat ttcccatccc ctgtgggaaa ttagtaggct catttactgt tttaggtcta    3780
gcctatgtgg attttttcct aacataccta agcaaaccca gtgtcaggat ggtaattctt    3840
attctttcgt tcagttaagt ttttcccttc atctgggcac tgaagggata tgtgaaacaa    3900
```

```
tgttaacatt tttggtagtc ttcaaccagg gattgtttct gtttaacttc ttataggaaa    3960
gcttgagtaa aataaatatt gtcttttgt atgtcaccca aaaaaaaaa                 4009
```

<210> SEQ ID NO 4
<211> LENGTH: 427
<212> TYPE: PRT
<213> ORGANISM: Homo sapiens

<400> SEQUENCE: 4

```
Met Glu Trp Pro Ala Arg Leu Cys Gly Leu Trp Ala Leu Leu Leu Cys
 1               5                  10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
            35                  40                  45

Ile Trp Thr Trp Asn Pro Pro Glu Gly Ala Ser Ser Asn Cys Ser Leu
 50                  55                  60

Trp Tyr Phe Ser His Phe Gly Asp Lys Gln Asp Lys Lys Ile Ala Pro
 65                  70                  75                  80

Glu Thr Arg Arg Ser Ile Glu Val Pro Leu Asn Glu Arg Ile Cys Leu
                 85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
                325                 330                 335

Gly Lys Lys Arg Asn Ser Thr Leu Tyr Ile Thr Met Leu Leu Ile Val
            340                 345                 350

Pro Val Ile Val Ala Gly Ala Ile Ile Val Leu Leu Leu Tyr Leu Lys
        355                 360                 365
```

```
Arg Leu Lys Ile Ile Ile Phe Pro Pro Ile Pro Asp Pro Gly Lys Ile
    370                 375                 380

Phe Lys Glu Met Phe Gly Asp Gln Asn Asp Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
            420                 425

<210> SEQ ID NO 5
<211> LENGTH: 420
<212> TYPE: PRT
<213> ORGANISM: Homo sapiens

<400> SEQUENCE: 5

Met Ile Ile Val Ala His Val Leu Leu Ile Leu Leu Gly Ala Thr Glu
1               5                   10                  15

Ile Leu Gln Ala Asp Leu Leu Pro Asp Glu Lys Ile Ser Leu Leu Pro
            20                  25                  30

Pro Val Asn Phe Thr Ile Lys Val Thr Gly Leu Ala Gln Val Leu Leu
        35                  40                  45

Gln Trp Lys Pro Asn Pro Asp Gln Glu Gln Arg Asn Val Asn Leu Glu
50                  55                  60

Tyr Gln Val Lys Ile Asn Ala Pro Lys Glu Asp Asp Tyr Glu Thr Arg
65                  70                  75                  80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
            100                 105                 110

Trp Ala Ser Ala Glu Leu His Ala Pro Pro Gly Ser Pro Gly Thr Ser
        115                 120                 125

Ile Val Asn Leu Thr Cys Thr Thr Asn Thr Thr Glu Asp Asn Tyr Ser
130                 135                 140

Arg Leu Arg Ser Tyr Gln Val Ser Leu His Cys Thr Trp Leu Val Gly
145                 150                 155                 160

Thr Asp Ala Pro Glu Asp Thr Gln Tyr Phe Leu Tyr Tyr Arg Tyr Gly
                165                 170                 175

Ser Trp Thr Glu Glu Cys Gln Glu Tyr Ser Lys Asp Thr Leu Gly Arg
            180                 185                 190

Asn Ile Ala Cys Trp Phe Pro Arg Thr Phe Ile Leu Ser Lys Gly Arg
        195                 200                 205

Asp Trp Leu Ser Val Leu Val Asn Gly Ser Ser Lys His Ser Ala Ile
210                 215                 220

Arg Pro Phe Asp Gln Leu Phe Ala Leu His Ala Ile Asp Gln Ile Asn
225                 230                 235                 240

Pro Pro Leu Asn Val Thr Ala Glu Ile Glu Gly Thr Arg Leu Ser Ile
                245                 250                 255

Gln Trp Glu Lys Pro Val Ser Ala Phe Pro Ile His Cys Phe Asp Tyr
            260                 265                 270

Glu Val Lys Ile His Asn Thr Arg Asn Gly Tyr Leu Gln Ile Glu Lys
        275                 280                 285

Leu Met Thr Asn Ala Phe Ile Ser Ile Ile Asp Asp Leu Ser Lys Tyr
290                 295                 300

Asp Val Gln Val Arg Ala Ala Val Ser Ser Met Cys Arg Glu Ala Gly
305                 310                 315                 320
```

-continued

```
Leu Trp Ser Glu Trp Ser Gln Pro Ile Tyr Val Gly Asn Asp Glu His
                325                 330                 335
Lys Pro Leu Arg Glu Trp Phe Val Ile Val Ile Met Ala Thr Ile Cys
                340                 345                 350
Phe Ile Leu Leu Ile Leu Ser Leu Cys Lys Ile Cys His Leu Trp
                355                 360                 365
Ile Lys Leu Phe Pro Pro Ile Pro Ala Pro Lys Ser Asn Ile Lys Asp
370                 375                 380
Leu Phe Val Thr Thr Asn Tyr Glu Lys Ala Gly Ser Ser Glu Thr Glu
385                 390                 395                 400
Ile Glu Val Ile Cys Tyr Ile Glu Lys Pro Gly Val Glu Thr Leu Glu
                405                 410                 415
Asp Ser Val Phe
                420

<210> SEQ ID NO 6
<211> LENGTH: 424
<212> TYPE: PRT
<213> ORGANISM: Mus musculus

<400> SEQUENCE: 6

Met Ala Arg Pro Ala Leu Leu Gly Glu Leu Leu Val Leu Leu Leu Trp
1               5                   10                  15
Thr Ala Thr Val Gly Gln Val Ala Ala Ala Thr Glu Val Gln Pro Pro
                20                  25                  30
Val Thr Asn Leu Ser Val Ser Val Glu Asn Leu Cys Thr Ile Ile Trp
                35                  40                  45
Thr Trp Ser Pro Pro Glu Gly Ala Ser Pro Asn Cys Thr Leu Arg Tyr
50                  55                  60
Phe Ser His Phe Asp Asp Gln Gln Asp Lys Lys Ile Ala Pro Glu Thr
65                  70                  75                  80
His Arg Lys Glu Glu Leu Pro Leu Asp Glu Lys Ile Cys Leu Gln Val
                85                  90                  95
Gly Ser Gln Cys Ser Ala Asn Glu Ser Glu Lys Pro Ser Pro Leu Val
                100                 105                 110
Lys Lys Cys Ile Ser Pro Pro Glu Gly Asp Arg Glu Ser Ala Val Thr
                115                 120                 125
Glu Leu Lys Cys Ile Trp His Asn Leu Ser Tyr Met Lys Cys Ser Trp
130                 135                 140
Leu Pro Gly Arg Asn Thr Ser Pro Asp Thr His Tyr Thr Leu Tyr Tyr
145                 150                 155                 160
Trp Tyr Ser Ser Leu Glu Lys Ser Arg Gln Cys Glu Asn Ile Tyr Arg
                165                 170                 175
Glu Gly Gln His Ile Ala Cys Ser Phe Lys Leu Thr Lys Val Glu Pro
                180                 185                 190
Ser Phe Glu His Gln Asn Val Gln Ile Met Val Lys Asp Asn Ala Gly
                195                 200                 205
Lys Ile Arg Pro Ser Cys Lys Ile Val Ser Leu Thr Ser Tyr Val Lys
                210                 215                 220
Pro Asp Pro Pro His Ile Lys His Leu Leu Leu Lys Asn Gly Ala Leu
225                 230                 235                 240
Leu Val Gln Trp Lys Asn Pro Gln Asn Phe Arg Ser Arg Cys Leu Thr
                245                 250                 255
Tyr Glu Val Glu Val Asn Asn Thr Gln Thr Asp Arg His Asn Ile Leu
                260                 265                 270
```

```
Glu Val Glu Glu Asp Lys Cys Gln Asn Ser Glu Ser Asp Arg Asn Met
            275                 280                 285

Glu Gly Thr Ser Cys Phe Gln Leu Pro Gly Val Leu Ala Asp Ala Val
        290                 295                 300

Tyr Thr Val Arg Val Arg Val Lys Thr Asn Lys Leu Cys Phe Asp Asp
305                 310                 315                 320

Asn Lys Leu Trp Ser Asp Trp Ser Glu Ala Gln Ser Ile Gly Lys Glu
                325                 330                 335

Gln Asn Ser Thr Phe Tyr Thr Thr Met Leu Leu Thr Ile Pro Val Phe
            340                 345                 350

Val Ala Val Ala Val Ile Ile Leu Leu Phe Tyr Leu Lys Arg Leu Lys
        355                 360                 365

Ile Ile Ile Phe Pro Pro Ile Pro Asp Pro Gly Lys Ile Phe Lys Glu
    370                 375                 380

Met Phe Gly Asp Gln Asn Asp Asp Thr Leu His Trp Lys Lys Tyr Asp
385                 390                 395                 400

Ile Tyr Glu Lys Gln Ser Lys Glu Glu Thr Asp Ser Val Val Leu Ile
                405                 410                 415

Glu Asn Leu Lys Lys Ala Ala Pro
            420

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
agaggaatta ccccctggatg                                              20

<210> SEQ ID NO 8
<211> LENGTH: 20
<212> TYPE: DNA
<213> ORGANISM: Artificial Sequence
<220> FEATURE:
<223> OTHER INFORMATION: synthesized anti-sense primer

<400> SEQUENCE: 8
tcaaggagct gctttcttca                                               20

<210> SEQ ID NO 9
<211> LENGTH: 21
<212> TYPE: DNA
<213> ORGANISM: Artificial Sequence
<220> FEATURE:
<223> OTHER INFORMATION: synthesized primer

<400> SEQUENCE: 9
gatccacttc ccaagaacag a                                             21

<210> SEQ ID NO 10
<211> LENGTH: 23
<212> TYPE: DNA
<213> ORGANISM: Artificial Sequence
<220> FEATURE:
<223> OTHER INFORMATION: synthesized primer

<400> SEQUENCE: 10
gatccgggcc cttttttttt ttt                                           23
```

```
<210> SEQ ID NO 11
<211> LENGTH: 6
<212> TYPE: PRT
<213> ORGANISM: Artificial Sequence
<220> FEATURE:
<223> OTHER INFORMATION: hypothetical variant sequence substituting
      for 8 c-termial amino acids of SEQ ID:2

<400> SEQUENCE: 11

Val Arg Cys Val Thr Leu
1               5

<210> SEQ ID NO 12
<211> LENGTH: 378
<212> TYPE: PRT
<213> ORGANISM: Artificial Sequence
<220> FEATURE:
<223> OTHER INFORMATION: SEQ ID NO. 2 synthesized with substitution
      of 8-C terminal amino acids with VRCTL

<400> SEQUENCE: 12

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300
```

```
                Cys Phe Val Val Arg Ser Lys Val Asn Ile Tyr Cys Ser Asp Asp Gly
                305                 310                 315                 320

Ile Trp Ser Glu Trp Ser Asp Lys Gln Cys Trp Glu Gly Glu Asp Leu
                                325                 330                 335

Ser Lys Lys Thr Leu Leu Arg Phe Trp Leu Pro Phe Gly Phe Ile Leu
                            340                 345                 350

Ile Leu Val Ile Phe Val Thr Gly Leu Leu Leu Arg Lys Pro Asn Thr
                        355                 360                 365

Tyr Pro Lys Met Val Arg Cys Val Thr Leu
                    370                 375

<210> SEQ ID NO 13
<211> LENGTH: 5
<212> TYPE: PRT
<213> ORGANISM: Artificial Sequence
<220> FEATURE:
<223> OTHER INFORMATION: hypothetical motif characteristic of family
      of SEQ ID NO. 2 and SEQ ID NO 4.
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Trp Ser Xaa Trp Ser
1               5

<210> SEQ ID NO 14
<211> LENGTH: 6
<212> TYPE: DNA
<213> ORGANISM: Artificial Sequence
<220> FEATURE:
<223> OTHER INFORMATION: synthetic polyadenylation signal

<400> SEQUENCE: 14 aataaa                                                                      6

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
aaaaaaaaaa aaagggcccg                                                      20

<210> SEQ ID NO 16
<211> LENGTH: 4
<212> TYPE: PRT
<213> ORGANISM: Artificial Sequence
<220> FEATURE:
<223> OTHER INFORMATION: synthesized C-terminal portion of
      [125I][Phe]-IL-13-GlyTyrGlyTyr.

<400> SEQUENCE: 16

Gly Tyr Gly Tyr
1
```

PURIFIED POLYPEPTIDES HAVING IL-13 RECEPTOR ACTIVITY

The present invention relates to purified polypeptides having a receptor activity specific for interleukin-13 (IL-13), to their biologically active fragments and to the corresponding nucleic acid sequences and to their applications.

IL-13 is a recently identified (1,2) cytokine of 112 amino acids secreted by the activated T lymphocytes, the B lymphocytes and the mastocytes after activation.

By virtue of its numerous biological properties shared with IL-4, IL-13 has been described as an IL-4-like cytokine. Its activities are indeed similar to those of IL-4 on the B cells (3-5), the monocytes (6-10) and other non-haematopoietic cells (11-12). On the other hand, contrary to IL-4, it would not exert a specific effect on resting or activated T cells (13).

Various biological activities of IL-13 on the monocytes/macrophages, the B lymphocytes and certain haematopoietic precursors have been described in detail by A. J. Minty, as well as in review articles on IL-13 (see for example 14). Several data indicate, in addition, that this cytokine has a pleiotropic effect on other cell types. These non-haematopoietic cells which are directly affected by IL-13 are endothelial and microglial cells, keratinocytes and kidney and colon carcinomas.

The anti-inflammatory and immunoregulatory activities of IL-13 may be useful, for example, in the treatment of autoimmune, tumour and viral pathologies.

An exploitation of these biological properties at the clinical level requires, however, a perfect knowledge of the signals and mechanisms via which these effects are exerted, so as to be able to control and modulate them in the relevant pathologies.

One of the stages in the analysis of the signal transmitted by a biological molecule within a cell consists in identifying its membrane receptor. The research studies carried out to this end on the IL-13 receptor have shown that IL-13 and IL-4 had a common receptor, or at the very least some of the components of a common receptor complex, as well as common signal transduction elements (15-18). This receptor is present at the surface of various cell types, in a variable number according to the cell type considered. The comparative distribution of the IL-13 and IL-4 receptors has been indicated by A. J. Minty (14).

Kondo et al. (19) have described the structure of a receptor having a high affinity for IL-4. This receptor is a dimer, formed by the association of a glycoprotein of 140 kDa (IL-4R) and of the γ chain of the IL-2 receptor (γc). IL-4 can bind to the glycoprotein subunit of 140 kDa (IL-4R or gp 140) with a high affinity (Kd between 50 and 100 pM) (15). However, this affinity is increased by a factor of 2 to 3 when the γc chain is associated with gp 140. This association is, in addition, necessary for the transmission of certain signals mediated by IL-4 (19, 20).

Cross-competition experiments for binding either of IL-13 or of IL-4 have demonstrated that IL-4 can normally prevent the binding of IL-13, whereas IL-13 can generally only partially prevent the binding of IL4 to its receptor (17,21) and does not attach to any of the two subunits of the IL-4 receptor or to the complex formed by their association. On the basis of these observations, the authors of the present invention have assumed that the receptor specific for IL-13 consisted of the receptor complex IL-4 associated with another IL-13 binding component (IL-13Rβ).

Research studies carried out on an erythroleukemic cell line capable of proliferating in response to IL-13 and IL-4 (TF-1 line) allowed them to show that these two cytokines produced similar intracellular events after attachment to their receptor (18). In parallel, cross-linking experiments allowed them to show that gp 140 could form heterodimers either with the γ chain, or with a new subunit, of a molecular weight of 55 to 70 kDa (17,21).

Moreover, research studies recently carried out on a mouse embryonic stem cell line have made it possible to isolate the genomic DNA and the cDNA encoding a polypeptide of 424 amino acid residues (IL-13Rα), suggesting that the IL-13 receptor shared with the IL-4 receptor a common chain so as to constitute a high-affinity receptor (22, 23), that is to say has an affinity whose constant Kd is situated between values of between about 10 pM and 100 pM (a low-affinity receptor having a constant Kd situated between the values of between 2 nM and 10 nM).

Given the importance, at the medical level, of the fine understanding of the phenomena of regulation of IL-4 and of IL-13, and in particular of the possibility of being able to separate and control separately the effects produced by either of these two cytokines, the authors of the present invention were interested on the one hand, in the characterization of a polypeptide specifically binding IL-13 with a high affinity and, on the other hand, in the characterization of another polypeptide which, alone, specifically binds IL-13 with a low affinity and which, if it is associated with the IL-4 receptor, constitutes a high-affinity receptor for IL-13.

These authors have now identified a human carcinoma cell line expressing the IL-13 specific receptor in a quantity greater than other known human renal carcinoma lines (21), and have now carried out the cloning of the primary subunit responsible for the attachment of IL-13 to the IL-4/IL-13 receptor, called IL-13Rβ, as well as the cloning of the common chain shared by the IL-13 receptor and the IL-4 receptor in order to constitute a high-affinity receptor which allows cross-competition between the 2 cytokines, called IL-13Rα. The present invention therefore relates to purified polypeptides specifically linking IL-13.

More particularly, the subject of the invention is purified polypeptides whose amino acid sequences correspond to that of a receptor specific for IL-13 (IL-13Rβ and IL-13Rα), or biologically active fragments thereof.

The subject of the invention is also isolated DNA sequences encoding the said polypeptides or their biologically active fragments.

It relates, in addition, to the expression vectors containing at least one of the nucleotide sequences defined above, and the host cells transfected with these expression vectors under conditions allowing the replication and/or expression of one of the said nucleotide sequences.

The methods for producing recombinant IL-13Rβ and IL-13Rα or their biological active fragments by the transfected host cells are also part of the invention.

The invention also comprises pharmaceutical compositions comprising IL-13Rβ and/or IL-13Rα or biologically active fragments thereof for the regulation of the immunological and inflammatory mechanisms produced by IL-13. It relates, in addition, to a method for the identification of agents capable of modulating the activity of IL-13Rβ and/or IL-13Rα, and the use of IL-R13β and/or IL-13Rα or of fragments thereof for screening these agents as well as for the manufacture of new products capable of modulating the activity of the IL-13 receptor.

The invention also comprises antibodies or derivatives of antibodies specific for IL-13Rβ and/or IL-13Rα.

Finally, it relates to a method of therapeutic treatment for modulating the immunological reactions mediated by IL-13, comprising the administration, to a patient, of IL-13Rβ and/ or IL-13Rα or of one of their biologically active fragments or of a compound capable of specifically modulating the activity of this receptor, in combination with a pharmaceutically acceptable vehicle.

In the description of the invention below, the following definitions are used:

polypeptide specifically binding IL-13 with a high affinity (IL-13Rβ): a polypeptide comprising the amino acid sequence SEQ ID No. 2 or any biologically active fragment or derivative thereof;

polypeptide which, alone, specifically binds IL-13 with a low affinity and which, if it is associated with the IL-4 receptor, constitutes a high-affinity receptor (IL-13Rα): a polypeptide comprising the amino acid sequence SEQ ID NO 4 or any biologically active fragment or derivative thereof;

biologically active: capable of binding specifically to IL-13 and/or of participating in the transduction of the signal specifically produced by IL-13 at the level of the cell membrane, and/or capable of interacting with the receptor specific for IL-4 (IL-4R/gp 140) so as to form a complex capable of binding IL-4 and IL-13, and/or which is recognized by antibodies specific to the polypeptide of sequence SEQ ID No. 2 and/or of sequence SEQ ID No. 4, and/or capable of inducing antibodies which recognize the polypeptide of sequence SEQ ID No. 2 and/or of sequence SEQ ID No. 4;

derivative: any polypeptide which is a variant of the polypeptide of sequence SEQ ID No. 2 and/or of sequence SEQ ID No. 4, or any molecule resulting from a modification of a genetic and/or chemical nature of the sequence SEQ ID No. 2 or of sequence SEQ ID No. 4, that is to say which is obtained by mutation, deletion, addition, substitution and/or chemical modification of one or of a limited number of amino acids, as well as any isoform sequence, that is to say a sequence which is identical to the sequence SEQ ID No. 2 or to the sequence SEQ ID No. 4, to one of their fragments or to one of their modified sequences, containing one or more amino acids in the D enantiomer form, the said variant, modified or isoform sequences having conserved at least one of the properties which make them biologically active.

The subject of the present invention is a purified polypeptide comprising an amino acid sequence chosen from:
a) the sequence SEQ ID No. 2 or the sequence SEQ ID No. 4,
b) any biologically active sequence derived from SEQ ID No. 2 or SEQ ID No. 4, according to the definition given above.

The manufacture of derivatives may have various objectives, including in particular that of increasing the affinity of the receptor for IL-13, that of modulating the cross-competition between IL-13 and IL-4, that of enhancing their levels of production, of increasing their resistance to proteases, of modifying their biological activity or of conferring new pharmaceutical and/or biological properties on them.

Among biologically active variants of the polypeptides as defined above, the fragments produced by alternate splicing of the transcripts (messenger RNAs) of the gene encoding one of the amino acid sequences described above are preferred.

In an advantageous variant, the 8 C-terminal amino acids of the polypeptide of SEQ ID NO:2 are substituted by the following 6 amino acids: VRCVTL (SEQ ID NO:11)

According to another advantageous aspect, the invention relates to a soluble form of IL-13Rβ, called IL-13Rβs, comprising especially the extracellular domain of the polypeptide of sequence SEQ ID No. 2 stretching up to residue 343 and preferably up to residue 337 as well as a soluble form of IL-13Rα, called IL-13Rαs, comprising especially the extracellular domain of the polypeptide of sequence SEQ ID No. 4 stretching up to residue 343 and preferably up to the residues between 336 and 342.

The polypeptide which comprises the sequence SEQ ID No. 2 or the sequence SEQ ID No. 4 represents a specific embodiment of the invention. As will emerge in the examples, this polypeptide may be expressed at the surface of human cells so as to form a functional IL-13 receptor and/or combine with the IL-4 receptor so as to form, with the γ chain of the IL-2 receptor, the receptor complex common to IL-4 and IL-13.

The subject of the present invention is also an isolated nucleic acid sequence, chosen from:
a) the sequence SEQ ID No. 1,
b) the sequence SEQ ID No. 3,
c) the nucleic acid sequences capable of hybridizing to the sequence SEQ ID No. 1 or to the sequence SEQ ID No. 3, or to their complementary sequences and encoding polypeptides having an IL-13 receptor activity, or allowing the reconstitution of a receptor having a high affinity for IL-13 and IL-4,
d) the nucleic acid sequences derived from the sequences a) and b) and c) because of the degeneracy of the genetic code.

More particularly, the subject of the invention is a sequence encoding the soluble part of IL-13Rβ or of IL-13Rα and any variant produced by alternate splicing of the transcripts of IL-13Rβ or of IL-13Rα, conserving at least one of the biological properties described.

A preferred embodiment is represented by a nucleic acid sequence comprising or consisting of the stretch of nucleotides stretching from nucleotide No. 1 up to nucleotide 1081, and preferably up to nucleotide 1063 on the sequence SEQ ID No. 1.

Another preferred embodiment is represented by a nucleic acid sequence comprising or consisting of the stretch of nucleotides stretching from nucleotide No. 1 up to nucleotide No. 1059, and preferably up to the nucleotides between numbers 1041 and 1056 on the sequence SEQ ID No. 3.

Advantageously, the nucleic acid sequence according to the invention is a sequence encoding a protein corresponding to the mature form of IL-13Rβ or of IL-13Rα, this mature protein being the result of the release of the signal peptide.

The various nucleotide sequences of the invention may be of artificial origin or otherwise. They may be DNA or RNA sequences obtained by screening sequence libraries by means of probes produced on the basis of the sequence SEQ ID No. 1 or of the sequence SEQ ID No. 3. Such libraries may be prepared by conventional molecular biology techniques known to persons skilled in the art.

The nucleotide sequences according to the invention may also be prepared by chemical synthesis or alternatively by a combination of methods including chemical or enzymatic modification of sequences obtained by screening of the libraries.

These nucleotide sequences allow the preparation of nucleotide probes encoding a polypeptide according to the invention or a biologically active fragment thereof. The appropriate hybridization conditions correspond to the temperature and ionic strength conditions customarily used by persons skilled in the art, preferably to temperature conditions of between $T_m-5°$ C. and $T_m-30°$ C. and still more preferably, to temperature conditions between $T_m-5°$ C. and $T_m-10°$ C. (high stringency), $T_m$ being the melting temperature, defined as the temperature at which 50% of the base-paired strands separate. Such probes are also part of the invention. They may be used as a IN VITRO diagnostic tool for the detection, by hybridization experiments, of transcripts specific for the polypeptides of the invention in biological samples or for the detection of aberrant syntheses or of genetic abnormalities resulting from a polymorphism, from mutations or from a poor splicing.

The probes of the invention comprise at least 10 nucleotides, and comprise at most the entire nucleotide sequence SEQ ID No. 1 or the entire nucleotide sequence SEQ ID No. 3 or their complementary strand.

Among the shortest probes, that is to say of about 10 to 15 nucleotides, the appropriate hybridization conditions correspond to the temperature and ionic strength conditions customarily used by persons skilled in the art.

Preferably, the probes of the invention are labelled prior to their use. For that, several techniques are within the capability of persons skilled in the art, such as for example fluorescent, radioactive, chemiluminescent or enzymatic labelling.

The IN VITRO diagnostic methods in which these nucleotide probes are used for the detection of aberrant syntheses or of genetic abnormalities, such as the loss of heterozygosity and genetic rearrangement, at the level of the nucleic sequences encoding an IL-13 receptor polypeptide or a biologically active fragment, are included in the present invention. Such a type of method comprises:

bringing a nucleotide probe of the invention into contact with a biological sample under conditions allowing the formation of a hybridization complex between the said probe and the above-mentioned nucleotide sequence, optionally after a preliminary step of amplification of the abovementioned nucleotide sequence;

detection of the hybridization complex which may be formed;

optionally, sequencing the nucleotide sequence forming the hybridization complex with the probe of the invention.

The cDNA probes of the invention may, in addition, be advantageously used for the detection of chromosomal abnormalities.

The nucleotide sequences of the invention are also useful for the manufacture and the use of sense and/or antisense oligonucleotide primers for sequencing reactions or for specific amplification reactions according to the so-called PCR (polymerase chain reaction) technique or any other variant thereof.

The nucleotide sequences according to the invention have, moreover, uses in the therapeutic field for the preparation of antisense sequences which are capable of hybridizing specifically with a nucleic acid sequence, including a messenger RNA, and may be used in gene therapy. The subject of the invention is thus antisense sequences capable of inhibiting, at least partially, the production of IL-13 receptor polypeptides as defined above. Such sequences advantageously consist of those which constitute the reading frame encoding IL-13Rβ or IL-13Rα at the level of the transcript.

They may be more particularly used in the treatment of allergies and of inflammation.

The nucleotide sequences according to the invention may, moreover, be used for the production of recombinant polypeptides, as defined above, having an IL-13 receptor activity.

These polypeptides may be produced from the nucleotide sequences defined above, according to techniques for the production of recombinant products known to persons skilled in the art. In this case, the nucleotide sequence used is placed under the control of signals allowing its expression in a cellular host. The cellular host used may be chosen from prokaryotic systems, such as bacteria, or from eukaryotic systems, such as yeasts, insect cells, CHO cells (chinese hamster ovary cells) or any other system which is advantageously available commercially. A cellular host preferred for the expression of the polypeptides of the invention consists of the fibroblast line COS-7 or COS-3.

The signals controlling the expression of the polypeptides, such as the promoters, the activators or the terminal sequences, are chosen according to the cellular host used. To this end, the nucleotide sequences according to the invention may be inserted into autonomously replicating vectors within the chosen host, or integrative vectors of the chosen host. Such vectors will be prepared according to the methods commonly used by persons skilled in the art, and the resulting clones may be introduced into an appropriate host by standard methods, such as for example electroporation.

The expression vectors containing at least one of the nucleotide sequences defined above are also part of the present invention.

In the case of the COS-7 or COS-3 cells, the transfection may be carried out using the vector pSE-1, as described in (17).

The invention relates, in addition, to the host cells transfected by these expression vectors. These cells may be obtained by the introduction, into host cells, of a nucleotide sequence inserted into a vector as defined above, followed by the culture of the said cells under conditions allowing the replication and/or expression of the transfected nucleotide sequence.

These cells may be used in a method for the production of a recombinant polypeptide of sequence SEQ ID No. 2 or SEQ ID No. 4 or a derivative, which method is itself included in the present invention and is characterized in that the transfected cells are cultured under conditions allowing the expression of a recombinant polypeptide of sequence SEQ ID No. 2 or SEQ ID No. 4, or a derivative, and in that the said recombinant polypeptide is recovered.

The purification processes used are known to persons skilled in the art. The recombinant polypeptide may be purified from cell lysates and extracts, from the culture supernatant, by methods used individually or in combination, such as fractionation, chromatographic methods, immunoaffinity techniques using specific mono- or polyclonal antibodies.

The mono- or polyclonal antibodies capable of specifically recognizing IL-13Rβ and/or IL-13Rα according to the definition given above are also part of the invention. Polyclonal antibodies may be obtained from the serum of an animal immunized against IL-13Rβ and/or IL-13Rα according to the usual procedures.

The monoclonal antibodies may be obtained according to the conventional hybridoma culture method described by Köhler and Milstein (Nature, 1975, 256, 495-497).

Advantageous antibodies are antibodies directed against the extracellular domain of IL-13Rβ and/or IL-13Rα.

The antibodies according to the invention are, for example, chimeric antibodies, humanized antibodies, Fab and F(ab')2 fragments. They may also exist in the form of labelled antibodies or immunoconjugates. For example, they may be associated with a toxin, such as the diphtheria toxin or with a radioactive product. These immunotoxins may in this case constitute therapeutic agents which may be used for the treatment of certain pathologies involving an overexpression of IL-13Rβ and/or IL-13Rα.

The antibodies of the invention, in particular the monoclonal antibodies, may also be used for the immunocytochemical analyses of the IL-13 receptors on specific tissue sections, for example by immunofluorescence or by gold or peroxidase labelling.

They may be advantageously used in any situation where the expression of IL-13Rβ and/or IL-13Rα needs to be observed, such as for example an abnormal over-expression or the monitoring of the regulation of membrane expression.

The invention therefore also relates to a process for the IN VITRO diagnosis of pathologies correlated with an abnormal expression of IL-13Rβ and/or of IL-13Rα, in biological samples capable of containing IL-13Rβ and/or IL-13Rα expressed at an abnormal level, characterized in that at least one antibody of the invention is brought into contact with the said biological sample, under conditions allowing the possible formation of specific immunological complexes between IL-13Rβ and/or of IL-13Rα and the said antibody (ies) and in that the specific immunological complexes which may be formed are detected.

The invention also relates to a kit for the IN VITRO diagnosis of an abnormal expression of IL-13Rβ and/or of IL-13Rα in a biological sample and/or for measuring the level of expression of the IL-13 receptor in the said sample comprising:

at least one antibody specific for IL-13Rβ and/or IL-13Rα, optionally attached onto a support, means for revealing the formation of specific antigen/antibody complexes between IL-13Rβ and/or IL-13Rα and the said antibody(ies) and/or means for quantifying these complexes.

Another subject of the invention relates to a method for the identification and/or isolation of ligands specific for IL-13Rβ and/or IL-13Rα or agents capable of modulating its activity, characterized in that a compound or a mixture containing various compounds, optionally nonidentified, is brought into contact with cells expressing at their surface IL-13Rβ and/or IL-13Rα, under conditions allowing interaction between the IL-13 receptor and the said compound, in the case where the latter would have an affinity for the receptor, and in that the compounds bound to IL-13Rβ and/or IL-13Rα, or those capable of modulating the biological activity thereof, are detected and/or isolated.

In a specific embodiment, this method of the invention is adapted to the identification and/or isolation of agonists and of antagonists of IL-13 for its IL-13Rβ and/or IL-13Rα receptor.

The invention also comprises pharmaceutical compositions comprising, as active ingredient, a polypeptide corresponding to the preceding definitions, preferably in a soluble form, combined with a pharmaceutically acceptable vehicle.

Such a polypeptide may indeed act in competition with IL-13Rβ and/or IL-13Rα expressed at the cell surface, and thereby constitute an antagonist specific for the binding of IL-13 to its receptor, which may be advantageously used for the synthesis of a medicinal product intended for modulating the reactions mediated by IL-13 in pathological situations.

Finally, the invention comprises a method for the therapeutic treatment of conditions linked to immunological reactions mediated by IL-13, comprising the administration to a patient of IL-13Rβ and/or IL-13Rα (or of one of their biologically active fragments), or of a compound capable of specifically modulating the biological activity thereof, in combination with a pharmaceutically acceptable vehicle.

Other characteristics and advantages of the invention will emerge in the rest of the description with the examples and the figures, of which the legends are represented below.

BRIEF DESCRIPTION OF THE DRAWINGS

FIG. 1: Characterization of the human IL-13Rβ receptor present in Caki-1 cells.

FIG. 2: Nucleotide sequence of the cDNA of IL-13Rβ (SEQ ID NO. 1), and comparison of the protein sequences of IL 5R (SEQ ID NO. 5) and IL-13Rβ (SEQ ID NO. 2).

FIGS. 2A & 2B nucleotide sequence of the cDNA of IL-13Rβ (SEQ ID NO. 1). The amino acids corresponding to the deduced signal peptide of the nucleic sequence are indicated in italics and those corresponding to the transmembrane domain are indicated in bold characters. The potential N-glycosylation sites (Asn-X-Ser/Thr) are underlined;

FIGS. 2C and 2D alignment of the amino acids of the IL-13Rβ (SEQ ID NO. 2) and IL-5R (SEQ ID NO. 5) sequences. The protein sequences of IL-13R (SEQ ID NO. 2) and IL-5R (SEQ ID NO. 5) are aligned as described above (24). The cysteine residues and the WSXWS (SEQ ID NO. 13) motif which are characteristic of this family of receptors are boxed.

FIG. 4 characterization of the recombinant IL-13Rβ receptor for IL-13. The COS-7 cells are transfected with IL-13Rβ cDNA and used for:

2036+sgt 2034: binding to cells transfected with 2036 in the presence of supernatant of cells transfected with 2034. 2036+ sgt pSE1: control

1274-20: in the presence of supernatant of CHO cells not expressing IL-13Rβs (control).

FIG. 7: Nucleotide sequence of the IL-13Rα (SEQ. ID NO. 3) cDNA and comparison of the protein sequences of human IL-13Rα (SEQ. ID NO. 4) and of murine IL-13Rα (SEQ. ID NO. 6).

FIGS. 7A, 7B, 7C & 7D Nucleotide sequence of the IL-13Rα (SEQ. ID NO. 3) cDNA. The amino acids corresponding to the signal peptide deduced from the nucleic sequence are underlined with a dotted line and those corresponding to the transmembrane domain are underlined with a double line. The potential N-glycosylation sites (Asn-X-Ser/Thr) are boxed.

FIGS. 7E & 7F Alignment of the amino acids of human IL-13Rα (SEQ. ID NO. 4) and of murine IL-13Rα (SEQ. ID NO. 6). The protein sequences of human IL-13Rα (SEQ. ID NO. 4) and of murine IL-13Rα (SEQ. ID NO. 6) are aligned as described above (24). The cysteine residues and the motif WSXWS (SEQ. ID NO. 3) which are characteristic of this family of receptors are boxed.

FIG. 8: Characterization of the recombinant IL-13Rβ.
The CHO or COS-3 cells transfected with the IL-13Rβ and/or IL-4R cDNA and used for:

FIGS. 8A & 8B Studies of the binding of iodine-125 labelled IL-13 by Scatchard analysis of the saturation curve with CHO cells transfected with IL-13Rβ cDNA (A), transfected with IL-13Rβ cDNA and IL-4R cDNA (B), transfected with IL-13Rβ cDNA (C) and transfected with IL-13Rβ cDNA and IL-4R cDNA (D), FIGS. 8A & 8B Competition experiments of binding of [125I]-IL-13 on CHO cells transfected with IL-13Rβ cDNA (E), transfected with IL-13Rβ cDNA and IL-4R cDNA (F), transfected with IL-13Rα cDNA (G) and transfected with IL-13Rα cDNA and IL-4R cDNA (H). The white and shaded columns represent respectively the specific binding of radiolabelled IL-13 in the presence of an excess (1,000 times more) of IL-13 or IL-4, the black columns represent total binding.

Figure 9:
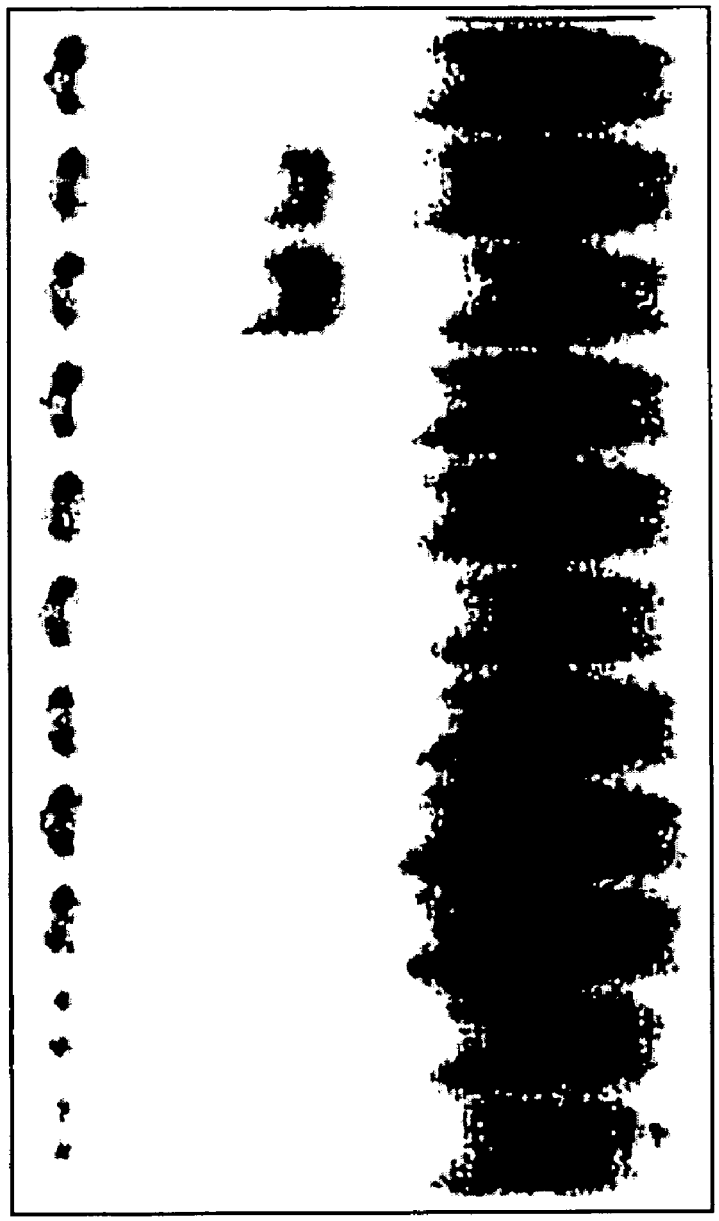

FIG. 9: Comparison of the electrophoretic mobility in EMSA of cellular extracts expressing the receptor for IL-4 alone (CHO-4), the receptor for IL-13Rα alone (CHO-13) or the combined receptors IL-13Rα and IL-4R (CHO-4-13) after activation of the CHO cells in the presence of IL-4 or IL-13 (4 or 13), c representing the nonactivated control.

MATERIALS AND METHODS

Binding and Cross-Linking Experiments

The binding an cross-linking experiments are carried out as described for [$^{125}$I][Phe43]-IL-13-GlyTyrGlyTyr (SEQ ID NO. 16) (17).

Induction of the Secretion of IL-6:
The Caki-1 cells (ATCC HTB46) are placed in 24-well plates at a density of $5 \times 10^4$ cells/well and after 3 days of culture, confluent monolayers are washed three times with DMEM medium without foetal calf serum. The stimulation of the Caki-1 cells is carried out with 30 ng/ml of IL-4 or of IL-13 in the absence or in the presence of Y124DIL-4 or of an anti-gp140 monoclonal antibody. The quantity of IL-6 released into the culture medium after incubating for 24 hours is measured by an ELISA technique (Innotest, France).

Isolation and Analysis of the Human IL-13Rβ cDNA:
Total RNA was extracted from the Caki-1 cells as described above (25). The poly(A) RNA is isolated from the total RNAs with magnetic beads coated with oligo(dT)$_{25}$ (Dynal). A cDNA library containing $2 \times 10^5$ clones was constructed using the primer-adaptor procedure (26) and the vector pSE-1 (27). The cloning strategy for the expression which was used has been previously described (17).

Preparation of Human IL-13Rβ cDNA:
The RNA samples are copied with reverse transcriptase and subjected to PCR (polymerase chain reaction) using a sense primer corresponding to the sequence +52 to +71 and an antisense primer corresponding to +489 to 470 (the numbering is made on the basis of the cDNA sequence shown in FIG. 2). The PCR-amplified products are hybridized with a probe complementary to sequences +445 to +461 of the cDNA. The size markers are indicated on the left of the figure.

Isolation and Analysis of the Human IL-13Rα cDNA:
1) Preparation of the Murine IL-13Rα Probe
a) Culture of the B9 Cells (28)
The B9 cells are cultured in RPMI medium (Gibco) supplemented with 10% foetal calf serum and 50 μg/ml of gentamycin.

b) Preparation of the RNA of the B9 Cells.
The cells are washed twice with PBS buffer (phosphate buffered saline, reference 04104040-GIBCO-BRL). After centrifugation for 10 min at 1000 rpm, the cellular pellet is suspended in the lysis buffer of the following composition: 4M guanidine-thiocyanate; 25 mM sodium citrate pH 7; 0.5% sarcosyl; 0.1 M β2-mercapto-ethanol.

The suspension is sonicated using an Ultraturax sonicator No. 231256 (JANKE and KUNDEL) at the maximum power for one minute. Sodium acetate pH 4 is added to 0.2 M. The solution is extracted with one volume of a phenol/chloroform mixture (v/v: 5/1).

The RNA contained in the aqueous phase is precipitated at −20° C. with the aid of one volume of isopropanol. The pellet is resuspended in the lysis buffer. The solution is again extracted with a phenol/chloroform mixture and the RNA is precipitated with isopropanol. After washing the pellet with 70% and then 100% ethanol, the RNA is resuspended in water.

c) Preparation of the Complementary DNA.
The cDNA is prepared from 5 μg of total RNA using a poly T12 primer. The total RNA is incubated in a volume of 30 μl of buffer: 50 mM Tris-HCl pH 8.3, 6 mM MgCl$_2$, 10 mM DTT, 40 mM KCl, containing 0.5 mM of each of the deoxynucleotide triphosphates and 30 units of Rnasin (Promega), for one hour at 37° C., and then for 10 minutes at 50° C., and then for a further 10 minutes at 37° C., with 200 units of the reverse transciptaze enzyme Rnase H (Gibco-BRL reference 8064A). The reaction is stopped by heating for 10 minutes at 65° C.

d) Specific Amplification of a Mouse IL-13Rα cDNA Fragment by the PCR Technique.
The polymerization is carried out with 6 μl of cDNA in 50 μl final volume with the buffer of the following composition: 10 mM Tris-HCl pH 8.3, 2.5 mM MgCl$_2$, 50 mM KCl, 4 dNTP 0.2 mM, 2 μg/ml of each of the two nucleic primers and 2.5 U of TAQ DNA polymerase (Beckman). The pairs of primers were chosen on the sequence published by Hilton (22).

Sense primer: nucleotide 249 to 268
5' AGAGGAATTACCCCTGGATG 3' (SEQ ID NO. 7)
Antisense primer: nucleotide 1256 to 1275
5' TCAAGGAGCTGCTTTCTTCA 3' (SEQ ID NO. 8)

The reaction is carried out for 30 cycles of 1 minute at 94° C., 1 minute at 58° C., 4 minutes at 72° C., followed by a final cycle of 10 minutes at 72° C.

e) Purification of the PCR Amplification Product.
After running on a 1% agarose gel (Sigma) in TAE buffer (40 mM, Tris-HCl, 1 mM EDTA pH 7.9) for 1 hour at 100 volts, the gel is stained in the presence of 1 μg/ml of ethidium bromide in the same buffer. The band corresponding to the amplification product (cDNA fragment of 1027 base pairs (bp) of IL-13Rα) is extracted using a Glass Max kit (Gibco).

f) Preparation of the Probe.
25 ng of the purified cDNA fragment of 1027 bp corresponding to the mouse IL-13Rα receptor are labelled with phosphorus-32 with the BRL Random Primers DNA labelling systems kit at a specific activity of $2.4\times10^9$ dpm/µg; alternatively, 100 ng are labelled by nick translation using the Boeringher kit at a specific activity of $4\times10^8$ dpm/µg.

2) Isolation and Analysis of the Human IL-13Rα cDNA a) Preparation of the Total RNA The total RNA was extracted from Caki-1 cells as described above in paragraph 1b.

b) Purification of the Messenger RNA (PolyA+ fraction)

The purification of the polyA+ fraction of the RNA is carried out using the DYNAL oligo $(dT)_{25}$ Dynabeads kit (reference 610.05) following the procedure recommended by the manufacturer. The principle is based on the use of superparamagnetic polystyrene beads onto which a poly$(dT)_{25}$ oligonucleotide is attached. The polyA+ fraction is hybridized with the oligo$(dT)_{25}$ oligonucleotide coupled to the beads which are trapped on a magnetic support.

c) Northern Blot.

5 µg of polyA+ messenger RNA are loaded on a 1% agarose, 8% formaldehyde denaturing gel in MOPS buffer (10 mM pH 7.4, 0.5 mM EDTA). After migration and transfer onto an N+ Hybond membrane (Amersham) in a 20×SSC buffer, the RNA is fixed by heating in an oven at 80° C. under vacuum. The membrane is then prehybridized for 2 hours at 42° C. in the following buffer: 1 M NaCl, 30% formamide; 1% SDS, 5× Denhart's; 100 µg/ml of salmon sperm DNA. After 2 hours of prehybridization, the membrane is hybridized in the same buffer with a concentration of mouse IL-13Rα probe prepared by random priming of $2.5\times10^6$ dpm/ml, for 16 hours. The membrane is then washed twice for 30 minutes in 2×SSC buffer 0.1% SDS at room temperature for 2 hours at 50° C. in the same buffer. After 4 days of exposure in a cassette (Molecular Dynamics), the Northern blot is analysed with an Instant Imager (Molecular Dynamics). A predominant transcript of 4200 bp and a doublet of 1500 bp and 2000 bp are detected in the Caki-1 cells, U373 and U937. Characterization of the Properties of the Human IL-13Rα and IL-13Rβ:

The COS-7 or CHO cells are transfected in Petri dishes as described above (17). 24 hours later, the cells are trypsinized and cultured in 24-well plates at a density of $8\times10^4$ cells/well. After culturing for 48 hours at 37° C., the cells are used for the binding experiments (assays carried out in triplicate show a variation of less than 10%) with iodinated IL-13 as described (17). For the transfection, the COS-7 or CHO cells were transfected in 25-cm² plates using 0.6 mg of various plasmids. After 24 hours, the cell monolayers are trypsinized and cultured in 12-well plates at $8\times10^4$ cells/well. Three days later, the binding and competition experiments are carried out with labelled IL-13 and with unlabelled IL-13 and/or IL-4. The results are representative of at least three experiments conducted independently.

Comparison of Electrophoretic Mobilities in EMSA of the Nuclear Extracts of the Cells Expressing the Human IL-13Rα and/or IL-4R:

$2\times10^6$ CHO cells are plated onto 10 cm Petri dishes. 24 hours later, the cells are transfected with 6 µg of plasmid DNA (34). After 48 hours, the cells are incubated at 37° C. for 30 minutes in 3 ml of medium with or without IL-13 or IL-4 at a concentration of 100 ng per ml. The cells are then rinsed twice with a PBS-0.5 mM EDTA buffer and then harvested in 1.2 ml of PBS. The cells are then centrifuged and the cellular extracts prepared as described in (35). The EMSAs are then carried out as described in (36) with 10 to 20 µg of cellular extracts and with an oligonucleotide probe radiolabelled with $^{32}$P (50,000-100,000 cpm), a probe corresponding to the Cε element of the human Cε promoter (37). The oligonucleotide probe synthesized has the following sequence:

5'-GATCCACTTCCCAAGAACAGA-3'.(SEQ ID NO. 9)

EXAMPLES

Example 1

Analysis of the Expression of Human IL-13Rβ at the Surface of Caki-1 Cells

Figure 1A:
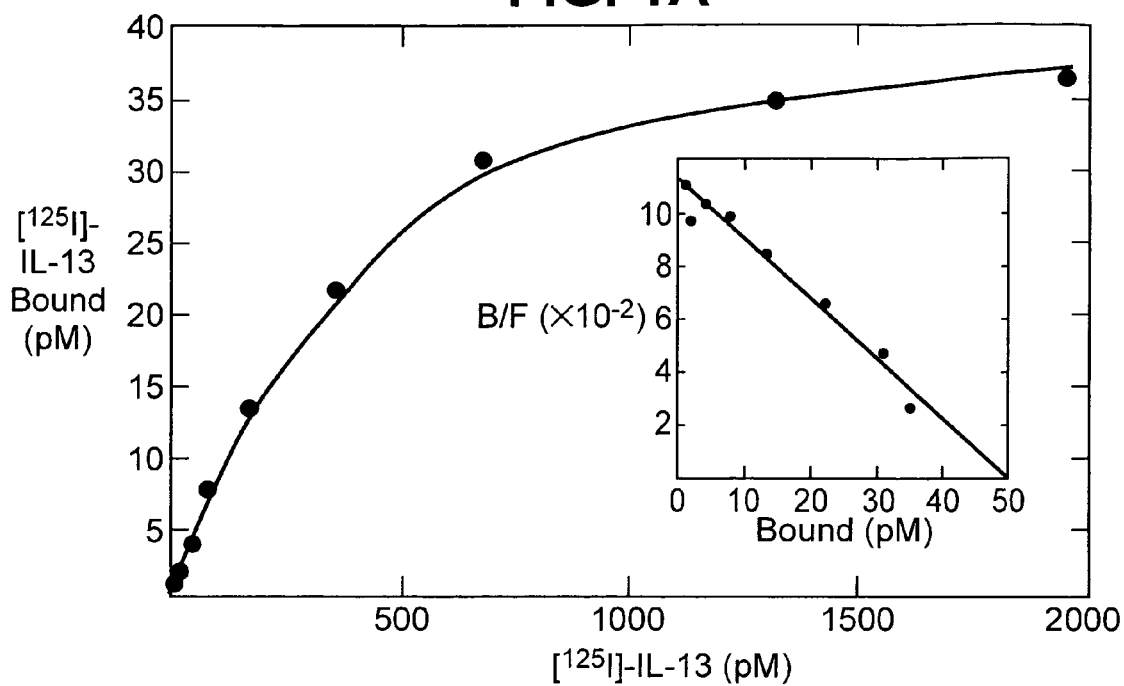
FIG. 1A Scatchard analysis (inset) of the saturation curve of IL-13 labelled with [$^{125}$I]
Figure 1B:
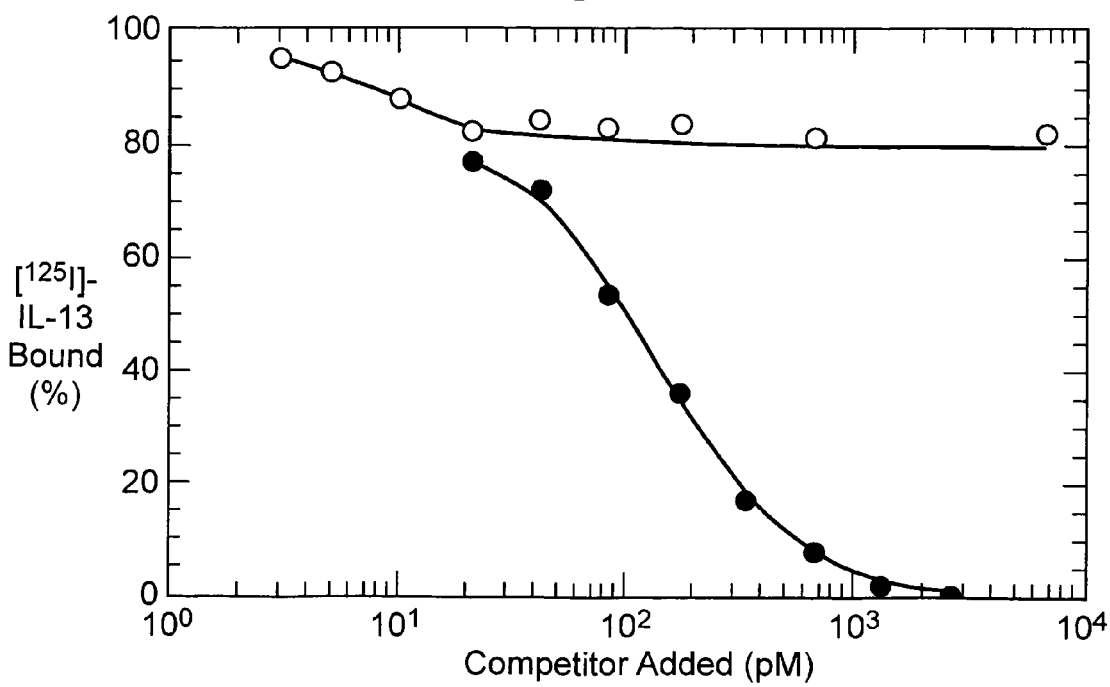
FIG. 1B binding of [$^{125}$I][Phe43]-IL-13-GlyTyrGlyTyr (SEQ ID NO. 16) in the presence of increasing concentrations of unlabelled IL-13 (.) and of IL-4 (o)

It was recently discovered that human renal carcinoma cells expressed, in addition to the receptors shared by IL-4 and IL-13, a large excess of specific IL-13 receptors (21). On the basis of these results, a sample of human carcinoma cell lines was studied for the attachment of IL-13 as described above (17). A specific line, Caki-1 (ATCC HTB46), which expresses a particularly large number of binding sites for IL-13, was analysed in greater detail. The Scatchard curves obtained from saturation experiments show the presence of binding sites with a Kd of 446±50 pM and a capacity of $7.2\times10^4$ receptors/cell (FIG. 1a). In competition experiments, unlabelled IL-13 completely displaces labelled IL-13 in a dose-dependent manner, whereas IL-4 displaces with a high affinity about 10% of the labelled IL-13. Higher concentrations of IL-4 (greater than 100 nM) do not displace the remaining 90% of bound IL-13 (FIG. 1b).

Figure 1C:
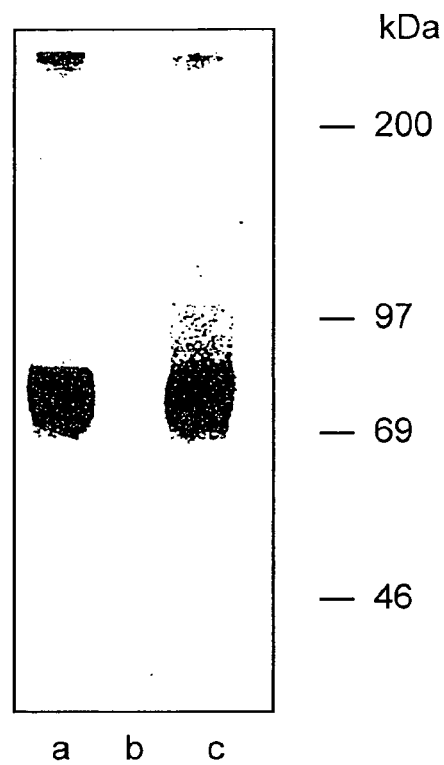
FIG. 1C cross-linking experiments using radioactive IL-13 in the absence (lane a) and in the presence of a one hundred times excess of unlabelled IL-13 (lane b) or of IL-4 (lane c)

These results are in agreement with the existence of two sites, one shared by the two cytokines, the other specific for IL-13. The experiments on cross-linking by affinity for IL-13 show a complex of about 70 kDa, which coincides with the complex observed in similar cross-linking experiments with IL-13 in various cell types (17,21). Labelled IL-13 is completely displaced from the complex by IL-13 but not by IL-4, which is in agreement with the competition experiments (FIG. 1c).

Example 2

Analysis of the Secretion of IL-6 Induced by IL-4 or IL-13

Figure 1D:
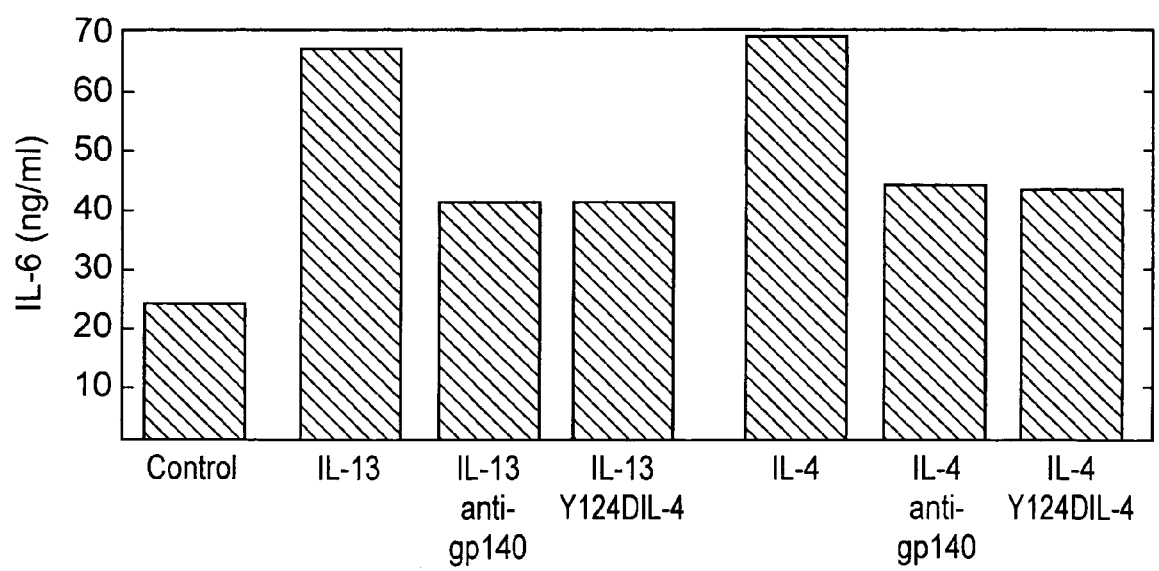
FIG. 1D inhibition of the secretion of IL-6 induced by IL-13 and IL-4 in the presence of a monoclonal antibody specific for the IL-4R chain and the IL-4 antagonist Y124DIL-4.

The authors of the invention analysed the secretion induced by IL-4 or IL-13 on Caki-1 cells. The two cytokines induce the secretion of similar levels of IL-6, and the secretion is inhibited by antibodies specific for the α chain of IL-4R and by the antagonist Y124DIL-4 (FIG. 1d). This suggests that the receptors shared by the two cytokines in the Caki-1 cells are responsible for the induction of the secretion of IL-6. Similar results are observed when the phosphorylation of the protein complex IRS1/4PS (18) induced by IL-4 and IL-13 is analysed in the presence or in the absence of anti-IL-4R antibodies and of IL-4 antagonist.

These results, taken as a whole, suggest that the receptor complex IL-4/IL-13 expressed in the Caki cells is identical to that which was previously described and that the protein binding IL-13 (IL-13Rβ) which is over-expressed is a component of the receptor responsible for the recognition of IL-13 in a functional complex which includes IL-4R. These cells were therefore used as source of messenger RNA for the cloning of this IL-13 binding entity.

Example 3

Cloning of the Primary Unit of the IL-13 Receptor (IL-13Rβ)

The strategy for the cloning and expression which was used has been previously described (17). A cDNA library containing 2×10⁵ recombinant clones was constructed (26) using Caki-1 cells. The library was divided into batches of 1000 cDNAs in which the DNA of each batch, in plasmid form, was introduced into COS-7 cells (29). The binding of labelled IL-13 to the transfected COS-7 cells makes it possible to identify the batches of clones encoding an IL-13 receptor. The positive batches were distributed out and rescreened until a single clone capable of carrying out the synthesis of a cell surface protein capable of binding IL-13 is identified. Two independent IL-13Rβ cDNAs were finally isolated. The complete nucleotide sequence of the IL-13Rβ cDNA and the amino acid sequence deduced therefrom are shown in FIGS. 2A and 2B. The cDNA has a length of 1298 bases excluding the poly-A tail and has a short 3' untranslated region of 106 bases. A canonical AATAAA (SEQ ID NO. 14) polyadenylation signal is in the expected place. The open reading frame between nucleotides 53 and 1192 defines a polypeptide of 380 amino acids. The sequence encodes a membrane protein with a potential signal peptide, a single transmembrane domain and a short intracytoplasmic tail.

Four potential N-glycosylation sites are located in the extracellular region. It is important to note that two consensus motifs considered as signatures of the type II family of cytokine receptors (30) are also present, the first being derived from an N-terminal disulphide bridge loop structure, the second being the WSXWS (SEQ ID NO. 13) type motif located at the C-terminal end of the extracellular region. The very short cytoplasmic sequence might explain why it is only the receptor complex shared by IL-4 and by IL-13 in the Caki cells which transduces a signal in the cell.

Alignment studies demonstrate homologies with the human IL-5R α chain (51% similarity and 27% identity, FIGS. 2C and 2D) and, to a lesser extent, with the prolactin receptor. It is interesting to note that the IL-5R complex consists of an α chain which binds IL-5 but which needs another protein, the β chain shared with the IL-3 and GM-CSF receptors, to form a high-affinity receptor which is capable of transducing a signal (31).

Example 4

Detection of the Human IL-13Rβ Messenger RNAs in Various Cell Lines

Figure 3:
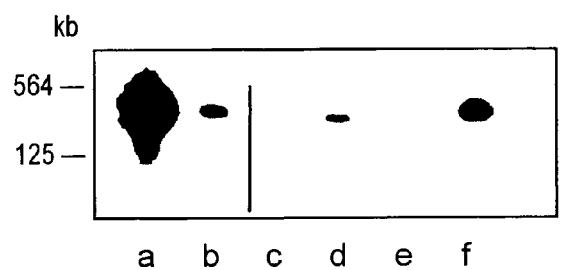
FIG. 3: Patterns of expression of the IL-13Rβ mRNA. The RNA was prepared from the following cells: Caki-1 (lane a), A431 (lane b), TF-1 (lane c), U937 (lane d), Jurkat (line e) and IM9 (lane f).

Surprisingly, in the Caki-1 cells, similar quantities of messenger RNAs for IL-13Rβ and IL-4R are detected by Northern analyses although a large excess of IL-13Rβ is expressed. This observation suggests that there is a greater translation of this mRNA compared with the IL-4R transcript and explains the lack of detection of the IL-13Rβ mRNA in the cell lines expressing a small number of IL-13 binding sites. RT-PCR analyses (FIG. 3) show that the transcript found in the Caki-1 cells is also present at lower levels in the keratinocytic line A431, the premyeloid cells TF-1, the premocytic cells U937 and the cell line B IM9. No transcript was detected in the Jurkat T cell line or in the pre-B NALM6 cell line. These results are in agreement with the IL-13 binding studies on these same lines previously described by the authors of the present invention (17), and with the known biological targets of IL-13.

Example 5

Binding Analyses Carried Out on COS-7 Cells Transfected with Human IL-13Rβ cDNA

Figure 4B:
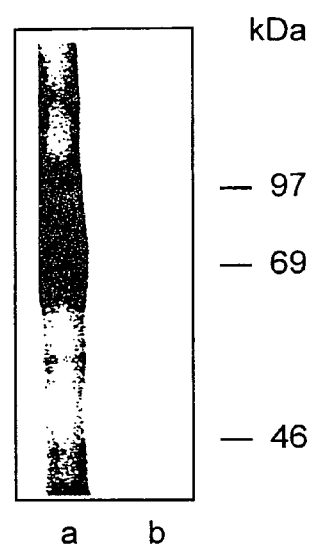
FIG. 4B cross-linking experiments using radiolabelled IL-13 in the absence (lane a) and in the presence of a one hundred times excess of unlabelled IL-13 (lane b)
Figure 4A:
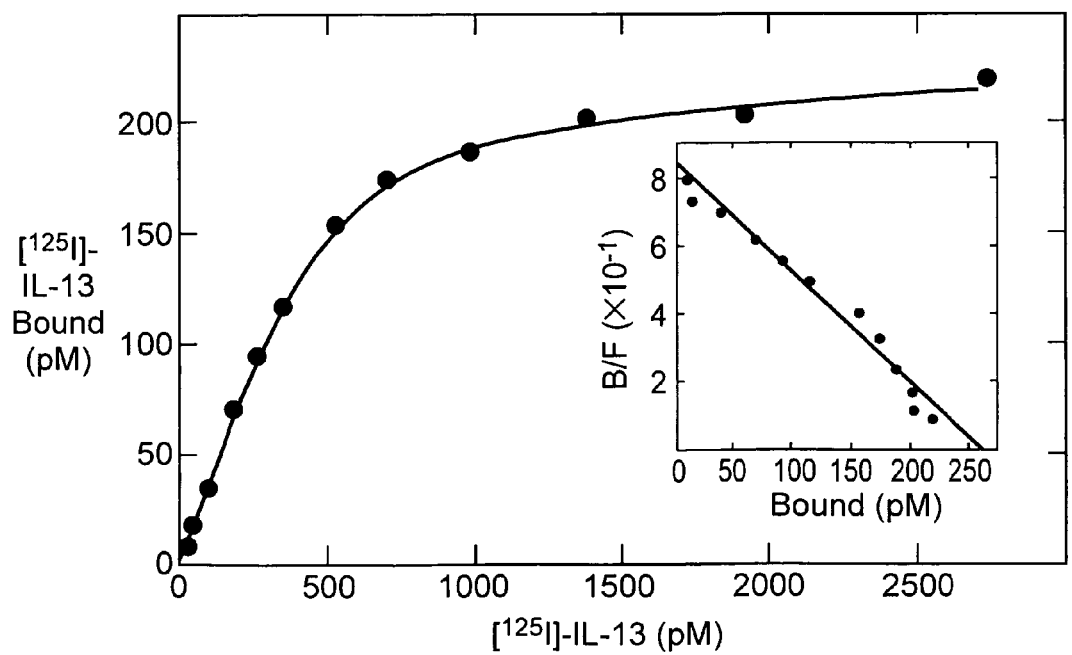
FIG. 4A studies for the binding of radiolabelled IL-13 (inset) by Scatchard analysis of the saturation curve.

The COS-7 cells transfected with the isolated cDNA encoding IL-13Rβ specifically bind labelled IL-13. The Scatchard analysis of the saturation curve shows a single component site with a Kd value of 250±30 pM and a maximum binding capacity of 5.6×10⁵ receptors/cell (FIG. 4a).

The affinity of the recombinant receptor is in good agreement with the Kd value of 446 pM for IL-13Rβ in the Caki-1 cells and for what has been described in several other cells (17). Consequently, in spite of a sequence homology with the α chain of IL-5R, the cloned receptor behaves differently since it does not need a second chain to reconstitute a high affinity binding site.

It is interesting to note that the protein binding IL-15 recently described likewise has the characteristic of binding IL-15 with a high affinity, in the absence of the other two components of the IL-15R complex (32).

In competition experiments, IL-13 is capable of inhibiting the binding of labelled IL-13 to the cloned receptor, with an inhibitory constant (Ki) of 1.5±0.5 nM, whereas IL-4 does not inhibit the binding. The pharmacology of the cloned receptor is therefore similar to that of the IL-13Rβ present in Caki-1 cells. Cross-linking experiments show a radiolabelled band of 70 kDa. This band has the same mobility as that observed in the Caki cells as well as in other cells (17). This complex most probably corresponds to the 60-70 kDa band observed in addition to the IL-4R 140 kDa band in cross-linking experiments carried out with labelled IL-4. This could also suggest that a strong interaction exists between the two proteins in the functional receptor complex. The authors of the present invention therefore checked if IL-13Rβ and IL-4R interact in the cell membrane to reconstitute a receptor which allows cross-competition between the two cytokines. The results of a coexpression experiment are shown in FIGS. 4 c and d.

It appears clearly that the expression of the two receptors, either separately or simultaneously, results in a large number of receptors which specifically recognize either of the two cytokines. However, when they are expressed together, a small number of receptors (5 to 10%) is capable of recognizing the two cytokines. The cotransfection of the γc chain with IL-4R and IL-13Rβ does not bring about an increase in the number of shared binding sites. These results suggest that the IL-13Rβ and IL-4R chains can interact with each other in the cell membrane to reconstitute a receptor for which IL-13 and IL-4 may be in competition. The low percentage of reconstituted receptors is an argument in favour of the presence of another protein (IL-13Rα) in limiting amounts in the COS cells which is necessary for the reconstitution of the receptor complex to which IL-13 and IL-4 bind competitively.

The results obtained in the transfection experiments with the γc chain demonstrate that this protein is not the limiting factor which was previously suggested (15). This conclusion is also supported by the absence of γc messenger RNA in the Caki-1 cells (21).

Another possible reason which explains the low number of reconstituted receptors is the existence of an incorrect stoichiometry of the two proteins in the cell membrane. However, cotransfections using different relative quantities of IL-4R and IL-13Rβ do not show a major difference in the number of reconstituted receptors. The possibility that another IL-13R with a greater capacity to interact with IL-4R exists was confirmed in mice (22) and in man by the isolation of the IL-13Rα cDNA (cf. EXAMPLE 7). It should be noted that the expression of γc enhances the binding of IL-4 as previously described (19) but reduces the binding of IL-13, suggesting a complex interaction between the different chains.

Example 6

Study of the Inhibition of the Binding of IL-13 to Its Membrane Receptor by a Receptor in Soluble Form The results in transient expression (FIG. 5) or on stable lines (FIG. 6) are described.

The two cDNA sequences encoding IL-13Rβ and IL-13Rβs are inserted into the vector p7055 in place of the IL-2 cDNA (33). The resulting plasmids are called 2036 and 2034 respectively.

a) Transient Expression

The CHO cells are inoculated into 12-well plates at 3×10⁵ cells/well and transfected the next day by the DEAE-Dextran method as for the COS cells, either with the plasmid 2036 or 2034, or with the empty plasmid pSE-1 as control.

The cells are cultured for three days so as to allow accumulation of IL-13Rβs in the supernatant of the cells transfected with the plasmid 2034 and good expression of IL-13Rβ in the membrane of the cells transfected with the plasmid 2036.

The supernatant of the cells transfected with IL-13Rβs (2034) or the negative control (empty pSE-1) is then collected and the cells transfected with IL-13Rβ are used to study the inhibition of the binding of IL-13.

The binding of IL-13 to the surface of the CHO cells expressing IL-13Rβ (2036) is measured in the presence or otherwise of these crude supernatants diluted one half with the radioligand or in the presence of an excess of nonradiolabelled IL-13 (NSB). The binding is carried out on whole cells in a final volume of 500 ml with 300 pM of radioligand, in triplicate.

b) Stable Lines

Two stable transformed CHO lines are obtained by transfection with the coding sequences of the complete IL-13Rβ (polypeptide of 380 residues) or of the IL-13Rβ in soluble form (IL-13Rβs, truncated polypeptide corresponding to residues 1 to 337 of IL-13Rβ). These sequences are inserted into the vector p7055.

The CHO-DHFR⁻ cells are transfected with the plasmids 2036 (IL-13Rβ) and 2034 (IL-13Rβs) and the recombinant clones selected as previously described (33).

One of the clones CHO-IL-13Rβ (CHO 2036) obtained, having 2 to 5×10⁵ sites per cell, is inoculated into a 12-well plate at a density of 10⁵ cells per well and the cells are used two days later for binding experiments in the presence or otherwise of IL-13Rβs.

For that, the CHO-IL-13Rβs (CHO 2034) clones are inoculated into 6 cm dishes, in triplicate, at 5×10⁵ cells per dish. After 3 days of accumulation in the culture medium, the medium (5 ml per dish) is collected for the IL-13 binding inhibition studies on IL-13Rβ of the CHO 2036 clone. In the same manner, the supernatant of CHO cells not expressing the soluble IL-13Rβ is collected.

The binding of IL-13 at the surface of the CHO 2036-22 clone is measured in the presence or otherwise of these crude supernatants diluted one half with the radioligand, or in the presence of an excess of nonradiolabelled IL-13 (NSB). The binding is carried out in triplicate, on whole cells, in a volume of 500 ml with 300 pM of radioligand.

Figure 5:
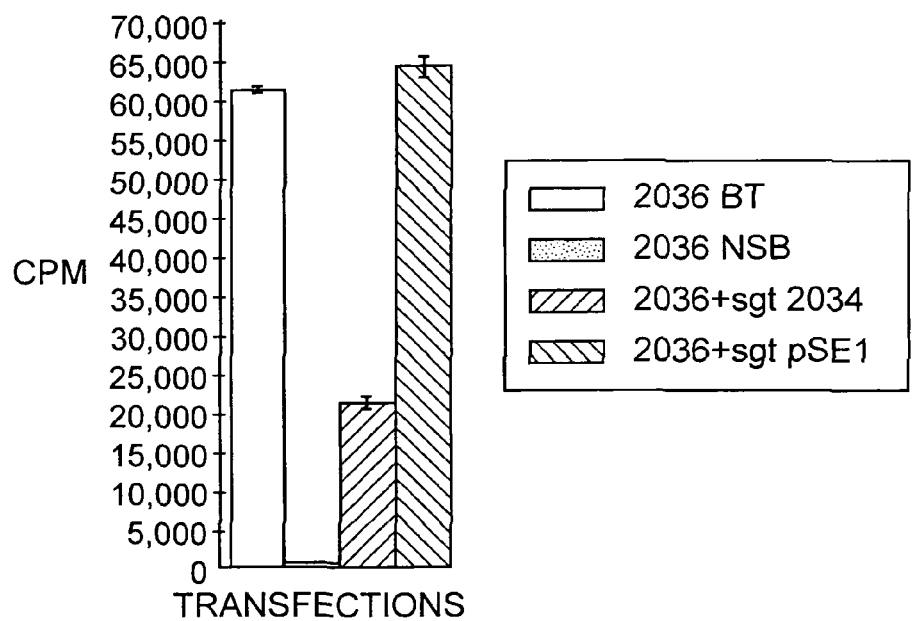
FIG. 5: inhibition of the binding of IL-13 to IL-13Rβ by the soluble form of the receptor (IL-13Rβs) in transient expression. The expression of IL-13Rβs in the supernatant of the cells transfected with 2034 is tested by inhibition of the binding of IL-13 on cells transfected with IL-13Rβ (2036). The supernatants are tested in the crude state by diluting them one half in the iodinated ligand. 2036 NSB: nonspecific binding in the presence of an excess of unlabelled IL-13. 2036 BT: total binding on cells transfected with 2036
Figure 6:
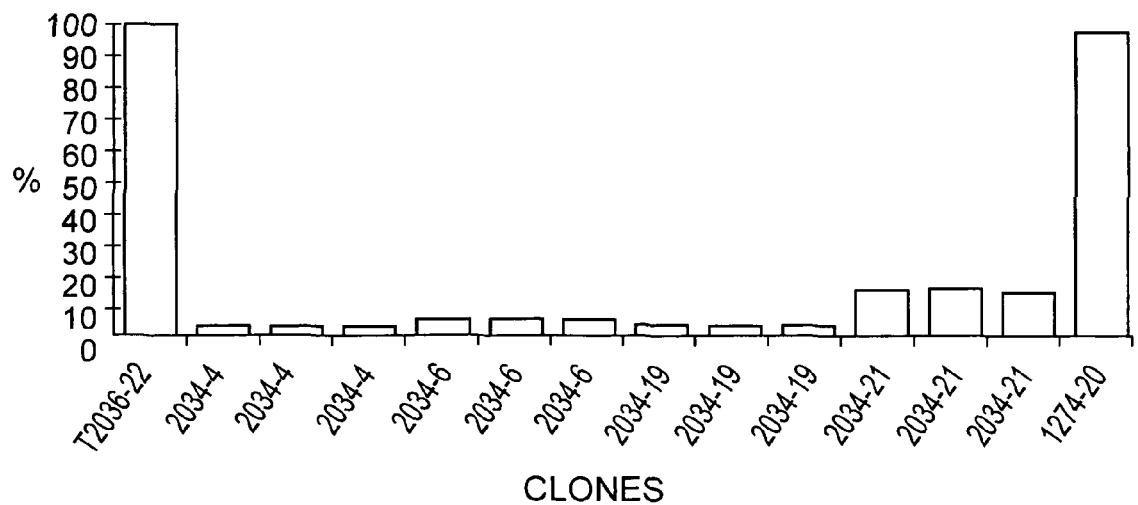
FIG. 6: Inhibition of the binding of IL-13 to IL-13Rβ by the soluble form of the receptor (IL-13Rβ) on stable lines. T2036-22: total binding on the clone IL-13Rβ (2036-22) in the absence of supernatant of clone secreting IL-13Rβs (reference 100%) 2034-4 2034-6 2034-19 4 clones IL-13Rβs 2034-21

The histograms of FIGS. 5 and 6 represent the inhibition of the binding of IL-13 on IL-13Rβ by IL-13Rβs. Inhibition of the binding of IL-13 to its receptor can be observed on several clones.

Example 7

Cloning of the Human IL-13Rα Receptor a) Preparation of the cDNA Library from PolyA+ Messenger RNAs of Caki-1 Cells Starting with 0.5 μg of polyA+ messenger RNA, single-stranded complementary DNA labelled with [³²P]dCTP (the complementary DNA obtained has a specific activity of 3000 dpm/ng) is prepared with the synthetic primer having the following sequence (comprising a BamHI site):

5' <GATCCGGGCCCTTTTTTTTTTTT <3' (SEQ ID NO. 10)

in a volume of 30 μl of the following buffer:
50 mM Tris-HCl pH 8.3, 6 mM MgCl₂, 10 mM DTT, 40 mM KCl, containing 0.5 mM of each of the deoxynucleic triphosphates, 30 μCi of [α³²P]dCTP and 30 U of Rnasin (Promega). After incubating for 1 hour at 37° C., and then for 10 minutes at 50° C. and then for a further 10 minutes at 37° C., with 200 units of the reverse transcriptase enzyme Rnase H (Gibco-BRL), 4 μl of EDTA are added. The RNA template is then degraded by adding 6 μl of a 2 N NaOH solution and incubating for 5 minutes at 65° C.

To remove the synthetic primer, the complementary DNA is purified on a 1 ml Sephacryl S400 column (Pharmacia), equilibrated in TE buffer. The first two radioactive fractions are combined and precipitated with a 1/10 volume of a 10 M ammonium acetate solution and 2.5 volumes of ethanol, this after extraction with chloroform. The cDNA is then extended in 5' by adding a dG homopolymeric tail with 20 units of terminal transferase enzyme (Pharmacia 27073001). Next, incubation is performed in 20 μl of buffer having the following composition: 30 mM Tris-HCl pH 7.6:1 mM cobalt chloride; 140 mM cacodylic acid; 0.1 mM DTT; 1 mM dGTP, for 15 minutes at 37° C., and then 2 μl of 0.5 M EDTA are added. A further treatment with sodium hydroxide is carried out without heating, followed by repurification on an S400 column, extraction with chloroform and precipitation with ethanol. The pellet is dissolved in 33 μl of TE buffer. The next stage consists in pairing the cloning vector pT7T3-18 through which a homopolymeric dC tail has been added beforehand after cutting with Pst1, the cDNA and the adaptor. The cDNA (33 μl) is brought into contact with 75 ng of vector pT7/T3-18 (5 μl), 120 ng of adaptor (1 μl) of the following sequence (comprising an Apa1 site),

5'AAAAAAAAAAAAGGGCCCG 3'

10 μl of a 200 mM NaCl solution, and the mixture is incubated for 5 minutes at 65° C. and then the reaction mixture is allowed to cool to room temperature. The next stage consists in ligating the cloning vector and the single-stranded cDNA in a reaction volume of 100 μl with 32.5 units of the enzyme T4 phage DNA ligase (Pharmacia) overnight at 15° C. in a buffer having the composition: 50 mM Tris-HCl pH 7.5; 10 mM MgCl₂, 1 mM ATP. The proteins are then removed by extraction with phenol followed by extraction with chloroform and then a 1/10 volume of a 10 mM ammonium acetate solution and 2.5 volumes of ethanol are added. The mixture is centrifuged, the pellet is taken up in the buffer having the composition: 33 mM Tris-acetate pH 7.9, 62.5 mM potassium acetate, 1 mM magnesium acetate and 1 mM DTT; the second cDNA strand is synthesized in a volume of 30 μl with 30 units of the enzyme T4 phage DNA polymerase (Pharmacia) and a mixture of 1 mM of the four deoxynucleotide triphosphates as well as two units of the protein of the T4 phage gene 32 (Pharmacia) for one hour at 37° C. The mixture is extracted with phenol and traces are removed by depositing on a P10 column (Biogel P10-200-400 mesh—reference 15011050—Biorad).

The last stage consists in transforming *E. Coli* MC 1061 cells by electroporation of the recombinant DNA using a Biorad Gene Pulser apparatus used at 2.5 kV under the conditions recommended by the manufacturer, and then the bacteria are cultured for one hour in LB medium having the composition:
bactotryptone 10 g/l; yeast extract 5 g/l; NaCl 10 g/l.

The number of independent clones obtained is determined by plating a 1/1000 dilution from the transformation after a one hour incubation on a dish of LB medium supplemented with 1.5% agar (w/v) and with 100 µg/ml of ampicillin called, in what follows, LB agar medium.

The number of independent clones obtained is 1 million.
b) Screening of the cDNA Library.

The entire library was plated on agar medium (Petri dishes 150 mm in diameter) coated with Biodyne A membranes (PALL reference BNNG 132). After leaving overnight at 37° C., the clones are transferred by contact onto new membranes. The latter are treated by placing them on Wathman 3 MM paper impregnated with the following solutions: 0.5 N NaOH, 1.5 M NaCl for 5 minutes and then 0.5 M Tris-HCl pH 8, 1.5 M NaCl for 5 minutes. After treatment with proteinase K in the following buffer, 10 mM Tris-HCl pH8, 10 mM EDTA, 50 mM NaCl, 0.1% SDS, 100 µg/ml proteinase K for 30 minutes at 37° C., the membranes are thoroughly washed in 2×SSC buffer (sodium citrate-NaCl), and then dried in an oven under vacuum at 80° C. for 20 minutes.
c) Prehybridization and Hybridization of the Membranes.

The membranes are then prehybridized for 2 hours at 42° C. in the following buffer: 1 M NaCl; 30% formamide; 1% SDS; 5× Denhart's 100 µg/ml of salmon sperm DNA. After 2 hours of prehybridization, the membranes are hybridized in the same buffer with a concentration of mouse IL-13Rα probe prepared by nick translation of $2.5 \times 10^6$ dpm/ml, for 16 hours. The membranes are washed for twice 30 minutes in 2×SSC, 0.1% SDS buffer at room temperature and then 2 hours at 50° C. in the same buffer. After overnight exposure at −80° C. in the presence of a Kodak X-OMAT film, several positive clones are detected.
d) Sequencing of a Human IL-13Rα Clone and Analysis of the Sequence.

The sequence is obtained using the Applied Biosystem kit (reference 401628). The complete nucleic sequence of the IL-13Rα cDNA and the amino acid sequence deduced therefrom are shown in FIGS. 7A-D. The cDNA is 3999 bases long excluding the poly-A tail and has a long untranslated 3' region of 2145 bases.

A canonical polyadenylation signal exists at the expected place. The open reading frame between nucleotides 34 and 1851 defines a polypeptide of 427 amino acids. The sequence encodes a membrane protein with a potential signal peptide and a single transmembrane domain and a short intracytoplasmic region.

10 potential glycosylation sites are located in the extracellular region. It is important to note that two consensus motifs considered as signatures of the type II family of cytokine receptors are also present, the first being derived from an N-terminal disulphide bridge loop structure, the second being the WSXWS type motif located at the C-terminal end of the extracellular region.

Example 8

Binding Analyses Carried Out on COS-3 or CHO Cells Transfected with Human IL-13Rα cDNA The CHO cells transfected with the isolated cDNA encoding IL-13Rα specifically bind labelled IL-13. The Scatchard analysis of the saturation curve shows a single component site with a Kd value of 4.5±0.4 nM and a maximum binding capacity of 26000 receptors/cell (FIGS. 8C and 8G).

The results of coexpression experiments are shown in FIGS. 8D and 8H.

Analysis of the results of FIG. 8C shows that IL-13Rα is well expressed in the clone 2036 of the CHO cells. It can be noted that IL-4R displaces 60% of the binding of IL-13 in the CHO cells cotransfected with IL-4R and IL-13Rα cDNA (FIG. 8H) but taking into account a Kd of 7.5 nM for IL-13Rα, there would be 10 times as many IL-13Rα sites as IL-4R sites.

The CHO-hIL4R cells (human IL-4R) expressing hIL-4R which are transfected with the cDNA encoding hIL-13Rα specifically bind labelled IL-13.

The Scatchard analysis of the saturation curve shows clearly 2 component sites, one of high affinity with a Kd value of 23±8.9 pM and a maximum binding capacity of 28000 sites/cell and the other of low affinity with a Kd value of 4.2±1.4 nM and a maximum binding capacity of 150000 sites/cell (FIG. 8D).

The second site characterized has the same affinity as hIL-13Rα (human IL-13Rα) expressed alone and corresponds to the nonassociated IL-13Rα chains because they are expressed in a larger quantity than hIL-4R.

These high-affinity receptors reconstituted in the presence of the 2 hIL-13Rα and hIL-4R chains are capable of recognizing the 2 cytokines (FIGS. 8D and 8H). This is even clearer on the COS/pSE1 cells coexpressing the 2 hIL-13Rα and hIL-4R chains in a comparable quantity where IL-4 displaces all the binding IL-13.

The affinity of the recombinant human IL-13Rα is comparable to that described for the mouse IL-13Rα receptor (2-10 nM) (ref. 22).

In contrast to the hIL-13Rβ chain previously described, human IL-13Rα does not constitute, on its own, a high-affinity binding site.

IL-13Rα and IL-4R therefore interact in the cell membrane to reconstitute a high-affinity receptor.

Example 9

Activation of the STAT Proteins by IL-13 and IL-4 in the CHO Cells Coexpressing hIL-13Rα and hIL-4R In human PBMC cells, hIL-4 and IL-13 activate 2 tyrosine kinases of the janus family, Jak1 and Jak2 which phosphorylate a latent transcription factor, STAT6. This activated factor enters the nucleus and binds to specific elements in the promoters of the genes regulated by IL-4.

We chose the Cε element of the human Cε promoter as probe in an electrophoretic mobility switch assay (EMSA) to demonstrate the activation by IL-13 of a binding factor similar to STAT6.

The nuclear extracts of the CHO cells, expressing IL-13R alone, IL-4R alone, or the 2 chains together, stimulated with 100 ng/ml of IL-13 or IL-4 for 30 min at 37° C., are incubated with the radiolabelled Cε element.

The nuclear extracts of the cells coexpressing hIL-13Rα and hIL-4R form a complex having the same mobility in EMSA whether the cells are induced with IL-4 or IL-13 (cf. FIG. 9). On the other hand, with the cells expressing either chain alone, no complex is detected.

In the CHO cells expressing hIL-13Rα and hIL-4Rα, IL-13 and IL-4 therefore initiate the same signalling cascade.

The cloning of IL-13Rβ and IL-13Rα described here makes it possible to improve the knowledge of the factors involved in the responses specifically induced by IL-13 compared with the responses induced by IL-4. It makes it possible, in addition, to have a tool for studying the regulation of the expression of the receptor under normal and pathological conditions where IL-13 plays a key role.

Moreover, the availability of cDNA makes it possible to facilitate the cloning of other proteins necessary for the reconstitution of an Il-4/IL-13 receptor complex and is also useful for the manufacture or the rational modelling of new medicinal products capable of being specific antagonists of the activities of IL-13.

REFERENCES

1. Minty, A. et al., Nature, 1993, 362, 248-250.
2. McKenzie, A. N. et al., Proc. Natl. Acad. Sci. U.S.A, 1993, 90, 3735-3739.
3. Defrance, T. et al., J. Exp. Med., 1994, 179, 135-143.
4. Punnonen, J. et al., Proc. Natl. Acad. Sci. (USA), 1993, 90, 3730-3734.
5. Fior, R. et al., Eur. Cytokine Network, 1994, 5, 593-600.
6. Muzio, M. R. F. et al., Blood, 1994, 83, 1738-1743.
7. De Waal Malefyt, R. et al., J. Immunol, 1993, 151, 6370-6381.
8. Doyle, A. et al., Eur. J. Immunol. 1994, 24, 1441-1445.
9. Montaner, L. J. et al., J. Exp. Med., 1993, 178, 743-747.
10. Sozzani, P. et al., J. Biol. Chem., 1995, 270, 5084-5088.
11. Herbert, J. M. et al., Febs Lett., 1993, 328, 268-270.
12. Derocq, J. M. et al., Febs Lett. 1994, 343, 32-36.
13. Zurawski, G. et al., Immunol. Today, 1994, 15, 19-26.
14. Interleukin-13 for Cytokines in Health and Disease. Eds D. G. Remick and J. S. Frie, Marcel Decker, N.Y. 1996.
15. Zurawski S. M. et al., Embo Journal, 1993, 12, 2663-2670.
16. Aversa, G. et al., J. Exp. Med., 1993, 178, 2213-2218.
17. Vita, N. et al., Biol. Chem., 1995, 270, 3512-3517.
18. Lefort, S. et al., Febs Lett., 1995, 366, 122-126.
19. Kondo, M. et al., Science, 1993, 262, 1874-1883.
20. Russell, S. M. et al., Science, 1993, 262, 1880-1883.
21. Obiri, N. et al., J. Biol. Chem., 1995, 270, 8797-8804.
22. Hilton, D. J. et al., Proc. Natl. Acad. Sci. USA, 1996, 93, 497-501.
23. Callard, R. E. et al., Immunology Today, 1996, 17, 3 108-110.
24. Devereux, J. et al., Nucleic Acids Res., 1984, 12, 387-395.
25. Chomczynski, P. et al., N. Anal. Biochem., 1987, 162, 156-159.
26. Caput, D. et al., Proc. Natl. Acad. Sci. USA, 1986, 83, 1670-1674.
27. Minty, A. et al., Eur. Cytokine Network, 1993, 4, 99-110
28. Labit Le Bouteiller, C. et al., J. of Immunol. Methods, 1995, 181, 1, 29-36.
29. Seed, B. et al., Proc. Natl. Acad. Sci. USA, 1987, 84, 3365-3369.
30. Bazan, J. F. et al., Proc. Natl. Acad. Sci. USA, 1990, 87, 6934-6938.
31. Honjo, T. et al., Current Opinion in Cell Biology, 1991, 1, 201-203.
32. Giri, J. G. et al., Embo Journal, 1993, 14, 3654-3663.
33. Miloux, B. et al., Gene, 1994, 149, 341-344.
34. Sampayrac, L. M. et al., PNAS USA, 1981, 78, 7575-7578.
35. Jiang, S-W et al., Nucleic Acid Res., 1995, 23, 3607-3608.
36. Köhler, I. et al., FEBS Letters, 1994, 345, 187-192.
37. Seidel, H. M. et al., PNAS USA, 1995, 92, 3041-3045.

The invention claimed is:

1. A purified polypeptide comprising the amino acid sequence of SEQ ID NO:4.

2. The purified polypeptide of claim 1 characterized in that it is a soluble form and comprises an amino acid sequence selected from the group consisting of:
    (a) residues 1-336 of SEQ ID NO:4;
    (b) residues 1-337 of SEQ ID NO:4;
    (c) residues 1-338 of SEQ ID NO:4;
    (d) residues 1-339 of SEQ ID NO:4;
    (e) residues 1-340 of SEQ ID NO:4;
    (f) residues 1-341 of SEQ ID NO:4;
    (g) residues 1-342 of SEQ ID NO:4; and
    (h) residues 1-343 of SEQ ID NO:4.

3. A composition comprising, as active ingredient, a purified polypeptide according to claims 1 or 2.

* * * * *

UNITED STATES PATENT AND TRADEMARK OFFICE
CERTIFICATE OF CORRECTION

| | | |
|---|---|---|
| PATENT NO. | : 7,928,073 B2 | Page 1 of 1 |
| APPLICATION NO. | : 11/182384 | |
| DATED | : April 19, 2011 | |
| INVENTOR(S) | : Daniel Caput et al. | |

It is certified that error appears in the above-identified patent and that said Letters Patent is hereby corrected as shown below:

In Drawings

Figure 4C:
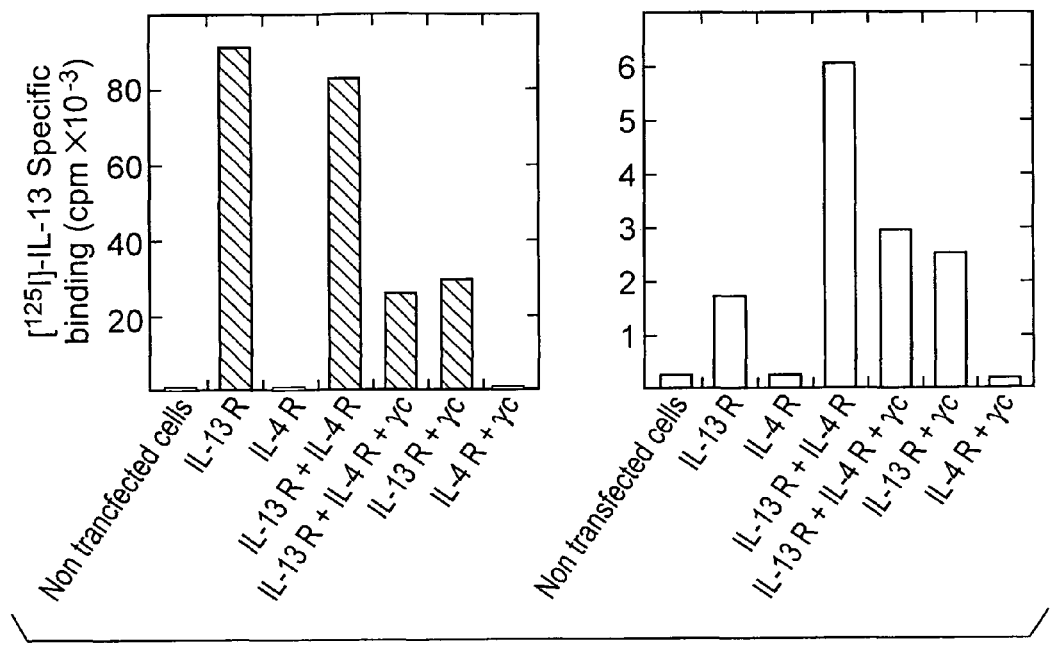
FIGS. 4C & 4D cotransfection experiments using cloned IL-13Rβ, IL 4R (gp140) and the gc chain followed by the binding of radiolabelled IL-13 (c) or of IL-4 (d). The black and white columns represent the specific binding of IL-13 and of IL-4 respectively.

On sheet 8 of 18, in Figure 4C, At the Bottom of Left graph, line 5, delete "trancfected" and insert -- transfected --, therefor.

Figure 4D:
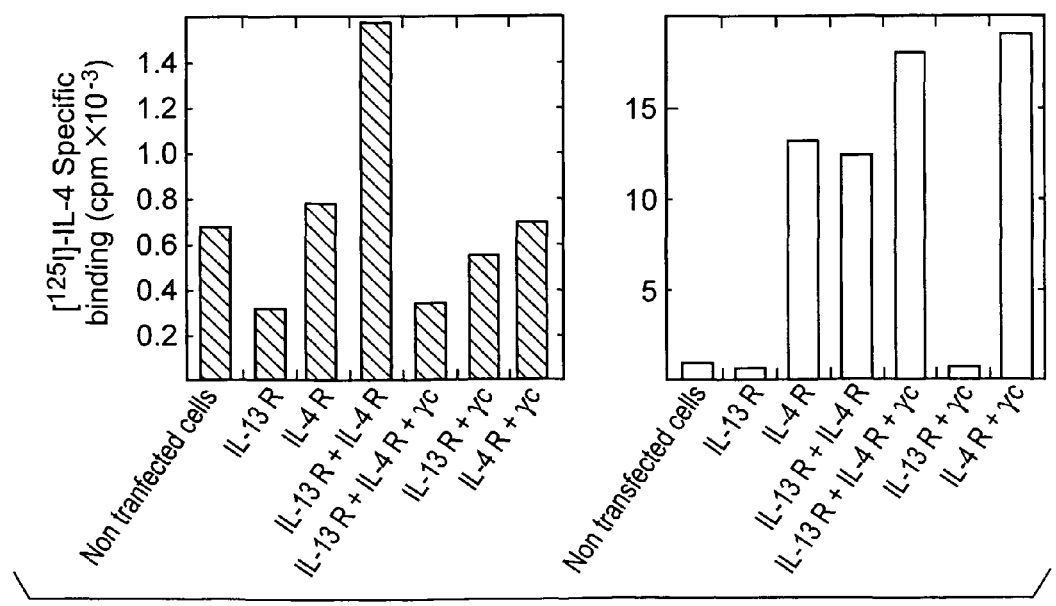

On sheet 8 of 18, in Figure 4D, At the Bottom of Left graph, line 8, delete "trancfected" and insert -- transfected --, therefor.

In column 8, line 55, delete "control" and insert -- control. --, therefor.

In column 9, line 43, delete "an" and insert -- and --, therefor.

In column 10, line 39, delete "transciptaze" and insert -- transcriptase --, therefor.

In column 11, line 3, delete "Boeringher" and insert -- Boehringer --, therefor.

In column 40, line 3, in claim 2, delete "(f" and insert -- (f) --, therefor.

Signed and Sealed this
Fifth Day of July, 2011

David J. Kappos
*Director of the United States Patent and Trademark Office*